US006927204B2

(12) United States Patent
Gao

(10) Patent No.: US 6,927,204 B2
(45) Date of Patent: Aug. 9, 2005

(54) TREATMENT OF INNER EAR HAIR CELLS

(75) Inventor: Wei-Qiang Gao, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 12 days.

(21) Appl. No.: 10/458,039

(22) Filed: Jun. 9, 2003

(65) Prior Publication Data

US 2003/0232759 A1 Dec. 18, 2003

Related U.S. Application Data

(60) Continuation of application No. 09/644,368, filed on Aug. 23, 2000, now Pat. No. 6,653,279, which is a division of application No. 08/963,596, filed on Oct. 31, 1997, now Pat. No. 6,156,728.
(60) Provisional application No. 60/029,536, filed on Nov. 1, 1996, and provisional application No. 60/030,278, filed on Nov. 4, 1996.

(51) Int. Cl.⁷ .................... A61K 38/00; A61K 38/28; A61K 39/395; C07K 16/00
(52) U.S. Cl. ................... 514/2; 514/3; 514/12; 530/303; 530/387.2; 530/388.2; 435/69.4; 435/810; 424/131.1; 424/145.1
(58) Field of Search .............. 514/2, 3, 12; 530/303, 530/387.2, 388.2; 435/69.4, 810; 424/131.1, 145.1

(56) References Cited

U.S. PATENT DOCUMENTS

| | | | |
|---|---|---|---|
| 3,773,919 A | 11/1973 | Boswell | |
| 4,485,045 A | 11/1984 | Regen | 424/19 |
| 4,544,545 A | 10/1985 | Ryan et al. | 424/88 |
| 4,637,402 A | 1/1987 | Adelman | 424/88 |
| 4,892,538 A | 1/1990 | Aebischer et al. | 128/746 |
| 5,011,472 A | 4/1991 | Aebischer et al. | 604/50 |
| 5,077,276 A | 12/1991 | Ballard et al. | 514/12 |
| 5,164,370 A | 11/1992 | Ballard et al. | 514/12 |
| 5,187,151 A | 2/1993 | Clark et al. | 514/12 |
| 5,229,271 A | 7/1993 | Philpott | 435/29 |
| 5,352,589 A | 10/1994 | Bergonzoni et al. | 435/29 |
| 5,407,913 A | 4/1995 | Sommer et al. | 514/3 |
| 5,464,943 A | 11/1995 | Senoo et al. | 514/12 |
| 5,470,828 A | 11/1995 | Ballard et al. | 530/399 |
| 5,482,929 A | 1/1996 | Fukunaga et al. | 514/12 |
| 5,514,566 A | 5/1996 | Fiddes et al. | 514/12 |
| 5,546,956 A | 8/1996 | Thornton | 128/746 |
| 5,843,749 A | * 12/1998 | Maisonpierre et al. | 435/194 |
| 6,133,231 A | 10/2000 | Ferrara et al. | 514/12 |
| 6,136,785 A | 10/2000 | Corwin et al. | 514/12 |
| 6,156,728 A | 12/2000 | Gas | 514/12 |
| 6,653,279 B1 | * 11/2003 | Gao | 514/2 |

FOREIGN PATENT DOCUMENTS

| | | |
|---|---|---|
| DE | 3218121 | 11/1983 |
| EP | 36676 | 9/1981 |
| EP | 52322 | 5/1982 |
| EP | 58481 | 8/1982 |
| EP | 88046 | 9/1983 |
| EP | 102324 | 3/1984 |
| EP | 128733 | 12/1984 |
| EP | 142641 | 5/1985 |
| EP | 143949 | 6/1985 |
| EP | 230869 | 8/1987 |
| EP | 288451 | 10/1988 |
| JP | 60-007934 | 1/1985 |
| WO | WO 87/01038 | 2/1987 |
| WO | WO 92/19195 | 11/1992 |
| WO | WO 93/10810 | 6/1993 |
| WO | WO 94/04030 | 3/1994 |
| WO | WO 95/05452 | 2/1995 |

OTHER PUBLICATIONS

Low, W., et al., "Basic Fibroblast Growth Factor (FGF–2) Protects Rat Cochlear Hair Cells in Organotypical Culture From Aminoglycoside Injury", *Journal of Cellular Physiology*—167(3):445–450 (1996).
Ernfors et al., "Protection of auditory neurons from aminoglycoside toxicity by neurotrophin–3", Nature Medicine, vol. 2, No. 4, pp. 463–467, Apr. 1996.
Staecker et al., "NT–3 combined with CNTF promotes survival of neurons in modioluis–spiral ganglion explants", NeuroReport vol. 6, No. 11, pp. 1533–1537, Jul. 1995.
Acheson et al., "A BDNF autocrine loop in adult sensory neurons prevents cell death" Nature 374:450–453 (1995).
Adler et al., "Immunocytochemical Evidence for Supporting Cell Conversion in the Acoustically Damaged Chick" *Assoc. Research Otolaryngology* (Abstract 16) pps. 4 (Feb. Meeting 1996).
Anderson, D. J., "The Neural Crest Cell Lineage Problem: Neuropolesis?" *Neuron* 3:1–12 (Jul. 1989).
Anniko et al., "Cisplatin: Evaluation of its Ototoxic Potential" *Am. J. Otolaryngol.* 7:276–293 (1986).
Apfel et al., "Nerve Growth Factor Prevents Toxic Neuropathy in Mice" *Annals of Neurology* 29(1):87–90 (Jan. 1991).
Ard et al., "Trophic Interactions Between the Cochleovestibular Ganglion of the Chick Embryo and its Synaptic Targets in Culture" *Neuroscience* 16(1):151–170 (1985).
Au et al., "Aminoglycoside Antibiotics Preferentially Increase Permeability in Phosphoinositide–containing Membranes: a Study with Carboxyfluoroscein in Liposomes" *Biochimica et Biophysica Acta* 902:80–86 (1987).

(Continued)

Primary Examiner—Jon Weber
Assistant Examiner—Abdel A. Mohamed
(74) Attorney, Agent, or Firm—Ginger R. Dreger; James A. Fox; Heller Ehrman White & McAuliffe LLP

(57) ABSTRACT

Compositions, methods, and devices are provided for inducing or enhancing the growth, proliferation, regeneration of inner ear tissue, particularly inner ear hair cells. In addition, provided are compositions and methods for prophylactic or therapeutic treatment of a mammal afflicted with an inner ear disorder or condition, particularly for hearing impairments involving hair cell damage, loss, or degeneration, by administration of a therapeutically effective amount of IGF-1 or FGF-2, or their agonists, alone or in combination.

7 Claims, 7 Drawing Sheets

OTHER PUBLICATIONS

Baird et al., "Cerebellar Target Neurons Provide a Stop Signal for Afferent Neurite Extension in vitro" *The Journal of Neuroscience* 12(2):619–634 (Feb. 1992).

Balak et al., "Regenerated hair cells can originate from supporting cell progeny: evidence from phototoxicity and laser ablation experiments in the lateral line system" *J. Neurosci* 10:2502–2512 (1990).

Barbacid, "The Trk Family of Neurotrophin Receptors: Molecular Characterization and Oncogenic Activation in Human Tumors" *Molecular Genetics of Nervous System Tumors* pps. 123–136 (1993).

Barde et al., "Purification of a New Neurotrophic Factor From Mammalian Brain" *EMBO Journal* 1(5):549–553 (1982).

Bareggi et al., "Gentamicin Ototoxicity: Histological and Ultrastructural Alterations After Transtympanic Administration" *Pharmacological Research* 22(5):635–644 (1990).

Barker et al., "Disruption of NGF Binding to the Low Affinity Neurotrophin Receptor $p^{75LNTR}$ Reduces NGF Binding to TrkA on PC12 Cells" *Neuron* 13:203–215 (1994).

Beck et al., "Igf1 Gene Disruption Results in Reduced Brain Size. CNS Hypomyelination. and Hippocampal Granule and Striatal Parvalbumin–Containing Neurons" *Neuron* 14:717–730 (Apr. 1995).

Berggren et al., "Intermediate Filament Proteins in the Embryonic Inner Ear of Mice Under Normal Conditions and After Exposure to Ototoxic Drugs" *Acta Otolaryngol* 109:57–65 (1990).

Berkemeier et al., "Neurotrophin–5: A Novel Neurotrophic Factor That Activates trk and trkB" *Neuron* 7:857–866 (Nov. 1991).

Bianchi et al., "Development of Auditory and Vestibular Neurons in Mice with a Targeted Disruption of the BDNF or NT–4 Gene" *Assoc. Research Otolaryngology* (Abstract 429) pps. 108 (Feb. Meeting 1996).

Boettcher et al., "Concentration of Salicylate in Serum and Perilymph of the Chinchilla" *Arch Otolaryngol Head Neck Surg.* 116:681–684 (1990).

Boettcher et al., "Effects of Sodium Salicylate on Evoked–response Measures of Hearing" *Hearing Research* 42:129–142 (1989).

Boettcher et al., "Salicylate Ototoxicity: Review and Synthesis" *Am. J. Otolaryngol.* 12:33–47 (1991).

Carenza et al., "Peripheral Neuropathy and Ototoxicity of Diclorodiamineplatinum: Instrumental Evaluation" *Gynecologic Oncology* 25:244–249 (1986).

Cattaneo et al., "Proliferation and Differentiation of Neuronal Stem Cells Regulated by Nerve Growth Factor" *Nature* 347:762–765 (1990).

Chao, "Gene Transfer and Molecular Cloning of the Human NGF Receptor" *Science* 232:518–521 (1986).

Chao, "Growth Factor Signaling: Where is the Specificity?" *Cell* 68:995–997 (Mar. 20, 1992).

Clary et al., "An Alternatively Spliced Form of the Nerve Growth Factor Receptor TrkA Confers an Enhanced Response to Neurotrophin 3" *Proc. Natl. Acad. Sci. USA* 91:11133–11137 (1994).

Clary et al., "TrkA Cross–linking Mimics Neuronal Responses to Nerve Growth Factor" *Molecular Biology of the Cell* 5:549–563 (1994).

Cohen et al., "Neurotrophin–4/5 (NT–4/5) Increases Adult Rat Retinal Ganglion Cell Survival and Neurite Outgrowth in vitro" *Journal of Neurobiology* 25(8):953–959 (1994).

Cordon–Cardo et al., "The trk Tyrosine Protein Kinase Mediates the Mitogenic Properties of Nerve Growth Factor and Neurotrophin–3" *Cell* 66:173–183 (Jul. 12, 1991).

Corwin et al., "Auditory Hair Cells: Structure, Function, Development, and Regeneration" *Annu. Rev. Neuroscience* 14:301–333 (1991).

Corwin et al., "Isolation of Pure Living Hair Cell Epithelia by Use of Thermolysin" *Assoc. Research Otolaryngology* (Abstract 345) pps. 87 (Feb. Meeting 1996).

Corwin et al., "Regeneration of Sensory Hair Cells After Acoustic Trauma" *Science* 240:1772–1774 (Jun. 24, 1988).

Cotanche et al., "Regeneration of Hair Cell Stereociliary Bundles in the Chick Cochlea Following Severe Acoustic Trauma" *Hearing Research* 30:181–196 (1987).

Cotanche et al., "Regeneration of Hair Cells in the Vestibulocochlear System of Birds and Mammals" *Current Opinion in Neurobiology* 4:509–514 (1994).

Davies et al., "Different Factors From the Central Nervous System and Periphery Regulate the Survival of Sensory Neurones" *Nature* 319:497–449 (1986).

Davies et al., "Neurotrophin–4/5 Is a Mammalian–specific Survival Factor for Distinct Populations of Sensory Neurons" *J. Neuroscience* 13(11):4961–4967 (Nov. 1993).

Davies et al., "p75–Deficient Trigeminal Sensory Neurons Have an Altered Response to NGF but Not to Other Neurotrophins" *Neuron* 11:565–574 (Oct. 1993).

Davis et al., "A Self–renewing Multipotential Stem Cell in Embryonic Rat Cerebral Cortex" *Nature* 372:263–266 (Nov. 17, 1994).

De Moura et al., "Salicylate Ototoxicity– A Human Temporal Bone Report" *Arch. Otolaryng.* 87:60–64(368–372) (1968).

Dublin, W., "Anatomic Principles With Some Functional and General Pathologic Applications" *Fundamentals of Sensorineural Auditory Pathology* (Chapter 3), Springfield, Illinois:Charles C. Thomas pps. 18–103.

Duckert et al., "Morphological Correlates of Functional Recovery in the Chicken Inner Ear After Gentamycin Treatment" *The Journal of Comparitive Neurology* 331:75–96 (1993).

Ernfors et al., "Complementary Roles of BDNF and NT–3 in Vestibular and Auditory Development" *Neuron* 14:1153–1164 (Jun. 1995).

Ernfors et al., "Function of the Neurotrophins in the Auditory and Vestibular Systems: Analysis of BDNF and NT–3 Gene Knockout Mice" *Assoc. Research Otolaryngology* (Abstract 759) pps. 190 (Feb. Meeting 1996).

Ernfors et al., "Mice Lacking Brain–derived Neurotrophic Factor Develop with Sensory Deficits" *Nature* 368:147–150 (Mar. 10, 1994).

Ernfors et al., "Molecular Cloning and Neurotrophic Activities of a Protein with Structural Similarities to Nerve Growth Factor: Developmental and Topographical Expression in the Brain" *Proc. Natl. Acad. Sci. USA* 87:5454–5458 (Jul. 1990).

Escandon et al., "Regulation of Neurotrophin Receptor Expression During Embryonic and Postnatal Development" *The Journal of Neuroscience* 14(4):2054–2068 (Apr. 1994).

Farinas et al., "Severe Sensory and Sympathetic Deficits in Mice Lacking Neurotrophin–3" *Nature* 369:658–661 (Jun. 23, 1994).

Finley et al., "Assessment of Growth Factor Effects on Dissociated Hair Cell Progenitors Cultured with a Feeder Layer" *Assoc. Research Otolaryngology* (Abstract 333), pps. 84 (Feb. Meeting 1996).

Fischer et al., "Reversal of Spatial Memory Impairments in Aged Rats by Nerve Growth Factor and Neurotrophins 3 and 4/5 but not by Brain–Derived Neurotrophic Factor" *Proc. Natl. Acad. Sci. USA* 91:8607–8611 (Aug. 1994).

Fleischman et al., "Ototoxicity of cis–Dichlorodiammine Platinum (II) in the Guinea Pig" *Toxicology and Applied Pharmacology* 33:320–332 (1975).

Forge et al., "Ultrastructural Evidence for Hair Cell Regeneration in the Mammalian Inner Ear" *Science* 259:1616–1619 (Mar. 12, 1993).

Frenz et al., "Induction of Chondrogenesis: Requirement for Synergistic Interaction of Basic Fibroblast Growth Factor and Transforming Growth Factor–beta" *Development* 120:415–424 (1994).

Fritzsch et al., "Mice Homozygous for a Non–functional trk–B Receptor Lack Selectively in the Innervation of Semicircular Canals" *Assoc. Research Otolaryngology* (Abstract 760) pps. 190 (Feb. Meeting 1996).

Fritzsch et al., "Reduction and Loss of Inner Ear Innervation in trkB and trkC Receptor Knockout Mice: A Whole Mount DiI and Scanning Electron Microscopic Analysis" *Auditory Neuroscience* 1:401–417 (1995).

Furley et al., "The Axonal Glycoprotein TAG–1 is an Immunoglobulin Superfamily Member with Neurite Outgrowth–Promoting Activity" *Cell* 61:157–170 (Apr. 6, 1990).

Gao et al., "Axon Extension and Retraction by Leech Neurons: Severing Early Projections to Peripheral Targets Prevents Normal Retraction of Other Projections" *Neuron* 1:269–277 (Jun. 1988).

Gao et al., "Cerebellar Granule Cell Neurogenesis is Regulated by Cell–Cell Interactions in Vitro" *Neuron* 6:705–715 (May 1991).

Gao et al., "Neurotrophin–3 Reverse Experimental Cisplatin–induced Peripheral Sensory Neuropathy" *Annals of Neurology* 38(1):30–37 (Jul. 1995).

Gao et al., "Neurotrophin–4/5 (NT–4/5) and Brain–Derived Neurotrophic Factor (BDNF) Act at Later Stages of Cerebellar Granule Cell Differentiation" *The Journal of Neuroscience* 15(4):2656–2667 (Apr. 1995).

Garner et al., "Isoforms of the Avian TrkC Receptor: A Novel Kinase Insertion Dissociates Transformation and Process Outgrowth From Survival" *Neuron* 13:457–472 (Aug. 1994).

Ghosh et al., "Distinct Roles for bFGP and NT–3 in the Regulation of Cortical Neurogenesis" *Neuron* 15:89–103 (1995).

Gotz et al., "Neurotrophin–6 is a New Member of the Nerve Growth Factor Family" *Nature* 372:266–269 (1994).

Gotz et al., "Production and Characterization of Recombinant Mouse Neurotrophin–3" *European Journal of Biochemistry* 204:745–749 (1992).

Gray et al., "IGF–1 Protects Hair Cells from Aminoglycoside–induced Apoptotic Cell Death" *Assoc. Research Otolaryncology* (Abstract 792) pps. 198 (Feb. Meeting 1996).

Guild et al., "Correlations of Differences in the Density of Innervation of the Organ of Corti with Differences in the Acuity of Hearing, Including Evidence as to the Location in the Human Cochlea of the Receptors for Certain Tones" *Acta Oto–Laryngologica*, Holmgren vol. XV:269–308 (1931).

Hefti, Franz, "Nerve Growth Factor Promotes Survival of Septal Cholinergic Neurons After Fimbrial Transections" *J. of Neuroscience* 6(8):2155–2162 (Aug. 1986).

Hinojosa, "Cochlear Neural Degeneration Without Hair Cell Loss in Two Patients With Aminoglycoside Ototoxicity" *The Journal of Infectious Diseases* 156(3):449–455 (1987).

Hohn et al., "Identification and Characterization of a Novel Member of the Nerve Growth Factor/Brain–derived Neurotrophic Factor Family" *Nature* 344:339–341 (Mar. 22, 1990).

Holley et al., "Monoclonal Antibody Markers for Early Development of the Stereociliary Bundles of Mammalian Hair Cells" *J. Neurocytology* 24:853–864 (1995).

Hood et al., "Contemporary Applications of Neurobiology in Human Hearing Assessment" *Neurobiology of Hearing: The Cochlea*, Altschuler et al., New York:Raven Press pps. 397–423 (1986).

Hyman et al., "BDNF is a Neurotrophic Factor for Dopaminergic Neurons of th Substantia nigra" *Nature* 350:230–233 (Mar. 21, 1991).

Hynes et al., "Neurotrophin–4/5 is a Survival Factor for Embryonic Midbrain Dopaminergic Neurons in Enriched Cultures" *Journal of Neuroscience Research* 37:144–154 (1994).

Ip et al., "Mammalian Neurotrophin–4: Structure, Chromosomal Localization, Tissue Distribution, and Receptor Specificity" *Proc. Natl. Acad. Sci. USA* 89:3060–3064 (Apr. 1992).

Ip et al., "Similarities and Differences in the Way Neurotrophins Interact with the Trk Receptors in Neuronal and Nonneuronal Cells" *Neuron* 10:137–149 (Feb. 1993).

Jarvis, J., "A Case of Unilateral Permanent Deafness Following Acetylsalicylic Acid" *J. Laryngology and Otology* 80(3):318–320 (Mar. 1966).

Johnson et al., "Structural and Functional Diversity in the FGF Receptor Multigene Family" *Advances in Cancer Research* 60:1–41 (1993).

Jones et al., "Molecular Cloning of a Human Gene That is a Member of the Nerve Growth Factor Family" *Proc. Natl. Acad. Sci. USA* 87:8060–8064 (1990).

Jones et al., "Regeneration of Sensory Cells after Laser Ablation in the Lateral Line System: Hair Cell Lineage and Macrophage Behavior Revealed by Time–Lapse Video Microscopy" *J. Neuroscience* 16(2):649–662 (Jan. 15, 1996).

Kaplan et al., "The trk Proto–Oncogene Product: A Signal Transducing Receptor for Nerve Growth Factor" *Science* 252:554–558 (Apr. 26, 1991).

Kaplan et al., "Tyrosine Phosphorylation and Tyrosine Kinase Activity of the trk Proto–oncogene Product Induced by NGF" *Nature* 350:158–160 (Mar. 14, 1991).

Kelley et al., "The Development Organ of Corti Contains Retinoic Acid and Forms Supernumerary Hair Cells in Response to Exogenous Retinoic Acid in Culture" *Development* 119:1041–1053 (1993).

Kelley et al., "Replacement of Hair Cells after Laser Microbeam Irradiation in Cultured Organs of Corti from Embryonic and Neonatal Mice" *J. Neuroscience* 15(4):3013–3026 (Apr. 1995).

Klein et al., "Expression of the Tyrosine Kinase Receptor Gene trkB is Confined to the Murine Embryonic and Adult Nervous System" *Development* 109:845–850 (1990).

Klein et al., "The trk Proto–Oncogene Encodes a Receptor for Nerve Growth Factor" *Cell* 65:189–197 (Apr. 5, 1991).

Klein et al., "The trkB Tyrosine Protein Kinase Is a Receptor for Brain–Derived Neurotrophic Factor and Neurotrophin–3" *Cell* 66:395–403 (Jul. 26, 1991).

Klein et al., "The trkB Tyrosine Protein Kinase Is a Receptor for Neurotrophin–4" *Neuron* 8:947–957 (May 1992).

Klein et al., "trkB, A Novel Tyrosine Protein Kinase Receptor Expressed During Mouse Neural Development" *EMBO Journal* 8(12):3701–3709 (1989).

Knusel et al., "Brain–derived Neurotrophic Factor Administration Protects Basal Forebrain Cholinergic but Not Nigral Dopaminergic Neurons from Degenerative Changes after Axotomy in the Adult Rat Brain" *The Journal of Neuroscience* 12(11):4391–4402 (Nov. 1992).

Koliatsos et al., "Evidence That Brain–Derived Neurotrophic Factor is a Trophic Factor for Motor Neurons in vivo" *Neuron* 10:359–367 (Mar. 1993).

Konings et al., "Reversal by NGF of Cytostatic Drug–induced Reduction of Neurite Outgrowth in Rat Dorsal Root Ganglia in vitro" *Brain Research* 640:195–204 (1994).

Kopf–Maier et al., "Changes in the Cytoskeleton Pattern of Tumor Cells by Cisplatin in vitro" *Chem–Biol. Interactions* 82:295–316 (1992).

Kopke et al., "Effect of Neurotrophic Factors on the Inner Ear: Clinical Implications" *Acta Oto–Laryngologica* 116(2):248–252 (Mar. 1996).

Kopke et al., "In vivo Treatment with TGFα/IGF–1/retinoic Acid Mixture Increases Hair Cell Regeneration/Repair in Guinea Pig Utricles" *Assoc. Research Otolaryngology* (Abstract 789) pps. 198 (Feb. Meeting 1996).

Korsching, "The Neurotrophic Factor Concept: A Reexamination" *The Journal of Neuroscience* 13(7):2739–2748 (1993).

Lamballe et al., "trkC, a New Member of the trk Family of Tyrosine Protein Kinases, Is a Receptor for Neurotrophin–3" *Cell* 66:967–979 (Sep. 6, 1991).

Lambert, P., "Inner Ear Hair Cell Regeneration in a Mammal: Identification of a Triggering Factor" *Laryngoscope* 104:701–718 (Jun. 1994).

Larkfors et al., "Effects of Neurotrophins on Rat Embryonic Cerebellar Purkinje Cells in Vitro" *Society for Neuroscience Abstracts* (Abstract 278.14) 19(Part 1):667 (1993).

Leake et al., "Chronic Intracochlear Electrical Stimulation in Neonatally Deafened Cats: Effects of Intensity and Stimulating Electrode Location" *Hearing Research* 64:99–117 (1992).

Lee et al., "Potential Role of bFGF and Retinoic Acid in the Regeneration of Chicken Cochlear Hair Cells" *Hearing Research* 94:1–13 (1996).

Lefebvre et al., "Neurotrophin Affect Survival and Neuritogenesis by Adult Injured Auditory Neurons in vitro" *NeuroReport* 5(8):865–868 (1994).

Lefebvre et al., "Regeneration and Mammalian Auditory Hair Cells" *Science* 267:707–711 (Feb. 3, 1995).

Lefebvre et al., "Retinoic Acid Stimulates Regeneration of Mammalian Auditory Hair Cells" *Science* 260:692–695 (Apr. 30, 1993).

Lefebvre et al., "Temporal Pattern or Nerve Growth Factor (NGF) Binding in vivo and the in vitro Effects of NGF on Cultures of Developing Auditory and Vestibular Neurons" *Acta Otolaryngol* 111:304–311 (1991).

Leibrock et al., "Molecular Cloning and Expression of Brain–derived Neurotrophic Factor" *Nature* 341:149–152 (Sep. 14, 1989).

Leon et al., "Insulin–like Growth Factor–I Regulates Cell Proliferation in the Developing Inner Ear, Activating Glycosyl–Phosphatidylinositol Hydrolysis and Fos Expression" *Endocrinology* 136(11):3494–3503 (1995).

Levi–Montalcini, R., "The Nerve Growth Factor: Thirty–five Years Later" *The EMBO Journal* 6(5):1145–1154 (1987).

Li et al., "Morphological Evidence for the Possibility of Direct Supporting Cell to Hair Cell Conversion in the Mature Mammalian Vestibular Sensory Epithelium" *ssoc. Research Otolaryngology* (Abstract 26) pps. 7 (Feb. Meeting 1996).

Li et al., "Multiple Factors Control the Proliferation and Differentiation of Rat Early Embryonic (Day 9) Neuroepithelial Cells" *Endocrine* 5(2):205–217 (Oct. 1996).

Lim, "Effects of Noise and Ototoxic Drugs at the Cellular Level in the Cochlea: A Review" *Am. J. Otolaryngol* 7(2):73–99 (Mar. 1996).

Lippe et al., "Loss of Avian Spiral Ganglion Neurons Following Aminoglycoside–induced Hair Cell Loss Regeneration" *Assoc. Research Otolaryngology* (Abstract 336) pps. 84 (Feb. Meeting 1996).

Low et al., "Basic fibroblast growth factor (FGF –2) protects rat cochlear hair cells in organotypical culture from aminoglycoside injury" *Biosis Database* (abstract only), Philadelphia, PA:Biosciences Information Service.

Low et al., "Protection of Cochlear Hair Cells form Aminoglycoside Injury by Basic Fibroblast Growth Factor (FGF–2)" *Assoc. Research Otolaryngology* (Abstract 797) pps. 200 (Feb. Meeting 1996).

Maisonpierre et al., "Neurotrophin–3: A Neurotrophic Factor Related to NGF and BDNF" *Science* 247:1446–1451 (Mar. 23, 1990).

Martin–Zanca et al., "Molecular and Biochemical Characterization of the Human trk Proto–Oncogene" *Molecular & Cellular Biology* 9(1):24–33 (Jan. 1989).

McAlpine et al., "The Ototoxic Mechanism of Cisplatin" *Hearing Research* 47:191–204 (1990).

McCabe et al., "The Effect of Aspirin Upon Auditory Sensitivity" *The Annals of Otology Rhinology & Laryngology* LXXIV(2):312–325 (1965).

Minichiello et al., "Differential Effects of Combined trk Receptor Mutations on Dorsal Root Ganglion and Inner Ear Sensory Neurons" *Development* 121:4067–4075 (1995).

Miranda et al., "Neuronal Colocalization of mRNAs for Neurotrophins and Thier Receptors in the Developing Central Nervous System Suggests a Potential for Autocrine Interactions" *Proc. Natl. Acad. Sci. USA* 90:6439–6443 (Jul. 1993).

Mollman, "Cisplatin Neurotoxicity" *New England J. of Medicine* 322(2):126–127 (Jan. 11, 1990).

Myers et al., "Salicylate Ototoxicity" *Arch Otolaryng* 82:483–493 (Nov. 1965).

Nakai et al., "Ototoxicity of the Anticancer Drug Cisplatin" *Acta Otolaryngol* 93:227–232 (1982).

Neff et al., "Insulin–like Growth Factors: Putative Muscle–derived Trophic Agents that Promote Motoneuron Survival" *J. Neurobiology* 24(12):1578–1588 (1993).

Oesterle et al., "bFGF Cell Proliferation in Cultured Inner–ear Sensory Epithelia" *Assoc. Research Otolaryngology* (Abstract 791) pps. 198 (Feb. Meeting 1996).

Oesterle et al., "Induction of cell proliferation in avian inner ear sensory epithelia by insulin–like growth factor–I and insulin" *Journal of Comparative Neurology* 380(2):262–274 (Apr. 7, 1997).

Pirvola et al., "Brain–derived Neurotrophic Factor and Neurotrophin 3 mRNAs in the Peripheral Target Fields of Developing Inner Ear Ganglia" *Proc. Natl. Acad. Sci. USA* 89:9915–9919 (1992).

Pirvola et al., "The Site of Action of Neuronal Acidic Fibroblast Growth Factor is the Organ of Corti of the Rat Cochlea" *Proc. Natl. Acad. Sci. USA* 92:9269–9273. (Sep. 1995).

Pryor, "Assessment of Auditory Dysfunction" *Principles of Neurotoxicology*, Louis W. Chang, New York:Marcel Dekker, Inc. pps. 345–371 (1994).

Raphael, Y., "Evidence for Supporting Cell Mitosis in Response to Acoustic Trauma in the Avian Inner Ear" *J. Neurocytology* 21:663–671 (1992).

Rastel et al., "An Original Organotypic Culture Method to Study the Organ of Corti of the Newborn Rat in vitro" *Journal of Neuroscience Methods* 47:123–131 (1993).

Reynolds et al., "Generation of Neurons and Astrocytes From Isolated Cells of the Adult Mammalian Central Nervous System" *Science* 255:1707–1710 (1992).

Richardson et al., "Cochlear Cultures as a Model System for Studying Aminoglycoside Induced Ototoxicity" *Hearing Research* 53:293–311 (1991).

Roelofs et al., "Peripheral Sensory Neuropathy and Cisplatin Chemotherapy" *Neurology* 34:934–938 (Jul. 1984).

Rosenthal et al., "Primary Structure and Biological Activity of a Novel Human Neurotrophic Factor" *Neuron* 4:767–773 (May 1990).

Ryals et al., "Hair Cell Regeneration After Acoustic Trauma in Adult Coturnix Quail" *Science* 240:1774–1776 (Jun. 24, 1988).

Rybak, L., "Ototoxic Mechanisms" *Neurobiology of Hearing: The Cochlea*, R.A. Altschuler, New York:Raven Press pps. 441–454 (1986).

Sans et al., "Analysis of Temporal and Spatial Patterns of Rat Vestibular Hair Cell Differentiation by Tritiated Thymidine Radioautography" *J. Comp. Neurology* 206:1–8 (1982).

Schacht, "Molecular Mechanisms of Drug–induced Hearing Loss" *Hearing Research* 22:297–304 (1986).

Schecterson et al., "Neurotrophin and Neurotrophin Receptor mRNA Expression in Developing Inner Ear" *Hearing Research* 73:92–100 (1994).

Sera et al., "Morphological Changes in the Vestibular Epithelia and Ganglion Induced by Ototoxic Drug" *Scanning Microscopy* 1(3):1191–1197 (1987).

Shelton et al., "Human trks: Molecular Cloning, Tissue Distribution, and Expression of Extracellular Domain Immunoadhesins" *The Journal of Neuroscience* 15(1):477–491 (1995).

Siegel et al., "Cisplatin–induced Peripheral Neuropathy" *Cancer* 66:1117–1123 (Sep. 15, 1990).

Snider, W., "Functions of the Neurotrophins During Nervous System Development: What the Knockouts Are Teaching Us" *Cell* 77:627–638 (Jun. 3, 1994).

Sobowicz et al., "Organotypic Development of the Organ of Corti in Culture" *Journal of Neurocytology* 4:543–572 (1975).

Soppet et al., "The Neurotrophic Factors Brain–Derived Neurotrophic Factor and Neurotrophin–3 Are Ligands for the trkB Tyrosine Kinase Receptor" *Cell* 65:895–903 (May 31, 1991).

Squinto et al., "TrkB Encodes a Functional Receptor for Brain–Derived Neurotrophic Factor and Neurotrophin–3 but Not Nerve Growth Factor" *Cell* 65:885–893 (May 31, 1991).

Stadnicki et al., "Cis–dichlorodiammineplatinum (II) (NSC–119875): Hearing Loss and Other Toxic Effects in Rhesus Monkeys" *Cancer Chemotherapy Reports* 59(3):467–480 (May/Jun. 1975).

Thompson et al., "Cisplatin Neuropathy: Clinical, Electrophysiologic, Morphologic, and Toxicologic Studies" *Cancer* 54:1269–1275 (1984).

Tsoulfas et al., "The Rat trkC Locus Encodes Multiple Neurogenic Receptors That Exhibit Differential Response to Neurotrophin–3 in PC12 Cells" *Neuron* 10:975–990 (May 1993).

Tsue et al., "Diffusible Factors Regulate Hair Cell Regeneration in the Avian Inner Ear" *Proc. Natl. Acad. Sci. USA* 91:1584–1588 (Feb. 1994).

Tsue et al., "Hair Cell Regeneration in the Inner Ear" *Otolaryngol Head Neck Surg.* 111:281–301 (1994).

Umemoto et al., "Hair cell regeneration in the chick inner ear following acoustic trauma: ultrastructural and immunohistochemical studies" *Cell & Tissue Research* 281(3):435–443 (Sep. 1995).

Valenzuela et al., "Alternative Forms of Rat TrkC with Different Functional Capabilities" *Neuron* 10:963–974 (May 1993).

Vazquez et al., "Pattern of trk B Protein–Like Immunoreactivity in vivo and in vitro Effects of Brain–derived Neurotrophic Factor (BDNF) on Developing Cochlear and Vestibular Neurons" *Anat. Embryol.* 189:157–167 (1994).

Verdi et al., "$p75^{LNGFR}$ Regulates Trk Signal Transduction and NGF–Induced Neuronal Differentiation in MAH Cells" *Neuron* 12:733–745 (Apr. 1994).

Vicario–Abejon et al., "Functions of Basic Fibroblast Growth Factor and Neurotrophins in the Differentiation of Hippocampal Neurons" *Neuron* 15:105–114 (Jul. 1995).

Von Bartheld et al., "Expression of Nerve Growth Factor (NGF) Receptors in the Developing Inner Ear of Chick and Rat" *Development* 113:455–470 (1991).

Warchol et al., "Regenerative Proliferation in Inner Ear Sensory Epithelia From Adult Guinea Pigs and Humans" *Science* 259:1619–1622 (Mar. 12, 1993).

Warchol et al., "Supporting Cells in Avian Vestibular Organs Proliferate in Serum–free Culture" *Hearing Research* 71:28–36 (1993).

Weisleder et al., "Hair Cell Regeneration in the Avian Vestibular Epithelium" *Experimental Neurology* 115:2–6 (1992).

Weskamp et al., "Evidence That Biological Activity of NGF is Mediated Through a Novel Subclass of High Affinity Receptors" *Neuron* 6:649–663 (Apr. 1991).

Wheeler et al., "Expression of BDNF and NT–3 mRNA in Hair Cells of the Organ of Corti: Quantitative Analysis in Developing Rats" *Hearing Research* 73:46–56 (1994).

Windebank et al., "The Effect of Nerve Growth Factor, Ciliary Neurotrophic Factor, and ACTH Analogs on Cisplatin Neurotoxicity in vitro," *Neurology* 44:488–494 (Mar. 1994).

Woodford et al., "Effects of Combinations of Sodium Salicylate and Noise on the Auditory Threshold" *Ann. Otol.* 87:117–127 (1978).

Yamashita et al., "Induction of Cell Prolferation in Mammalian Inner–ear Sensory Epithelia by Transforming Growth Factor α and Epidermal Growth Factor" *Proc. Natl. Acad. Sci. USA* 92:3152–3155 (1995).

Yan et al., "Brain–derived Neurotrophic Factor Rescues Spinal Motor Neurons From Axotomy–induced Cell Death" *Nature* 360:753–755 (1992).

Yan et al., "Distribution of Intracerebral Ventricularly Administered Neurotropins in Rat Brain and Its Correlation with Trk Receptor Expression" *Experimental Neurology* 127:23–36 (1994).

Ylikoski et al., "Expression Patterns of Neurotrophin and Their Receptor mRNA in the Rat Inner Ear" *Hearing Research* 65:69–78 (1993).

Zheng et al., "Differential Damage to Auditory Neurons and Hair Cells by Ototoxins and Neuroprotection by Specific Neurotrophins in Rat Cochlear Organotypic Culture" *Eur. J. Neuro.* 8:1897–1905 (1996).

Zheng et al., "Fibroblast and insulin–like growth factors stimulate proliferation of rat utricular epithelial cells in vitro" *Society for Neuroscience Abstracts* (26th Annual Meeting, Wash D.C. Nov. 16–21, (1996) 22(1–3):1620 (1996).

Zheng et al., "Fibroblast and insulin–like growth factors stimulate proliferation of rat utricular epithelial cells in vitro" *Biosis Database* (abstract only), Philadelphia, PA:Biosciences Information Service.

Zheng et al., "Induction of cell proliferation by fibroblast and insulin–like growth factors in pure rat inner ear epithelial cell cultures" *Journal of Neuroscience* 17(1):216–226 (Jan. 1, 1997).

Zheng et al., "Neurotrophin–4/5 Enhance Survival of Cultured Spiral Ganglion Neurons and Protects Them From Cisplatin Neurotoxicity" *The Journal of Neuroscience* 15(7):5079–5087 (Jul. 1995).

Zheng et al., "Neurotrophin–4/5, Brain–Derived Neurotrophic Factor, and Neurotrophin–3 Promote Survival of Cultured Vestibular Ganglion Neurons and Protect Them Against Neurotoxicity of Ototoxins" *Journal of Neurobiology* 28(3):330–340 (1995).

\* cited by examiner

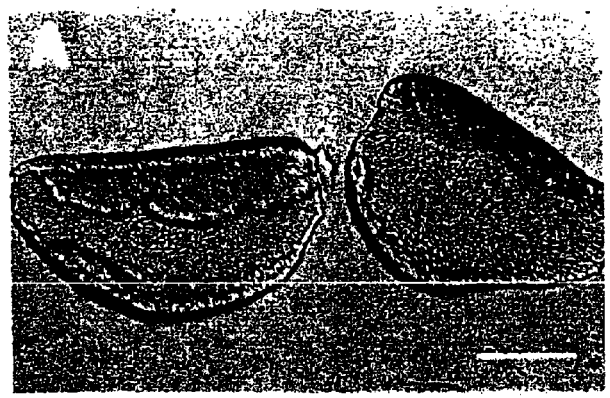
FIG._1A
FIG._1B
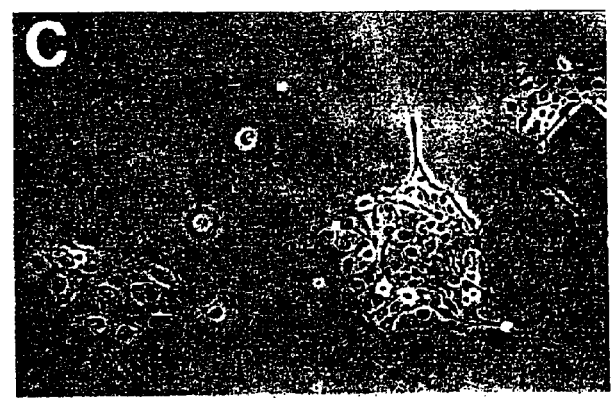
FIG._1C
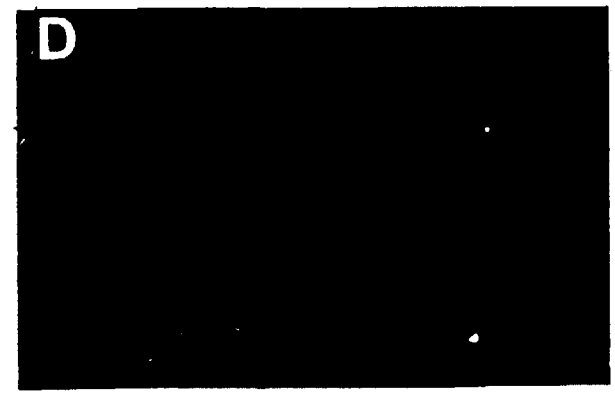
FIG._1D

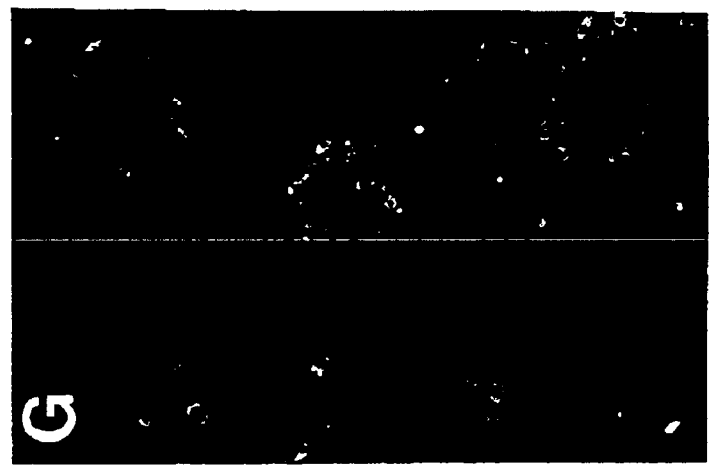
FIG._1G
FIG._1F
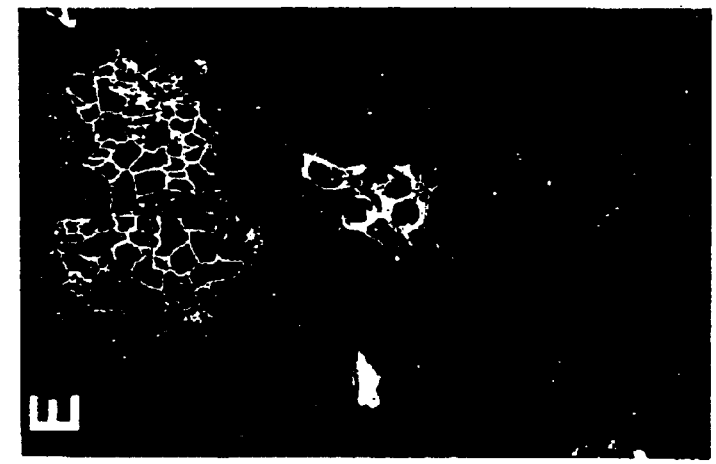
FIG._1E

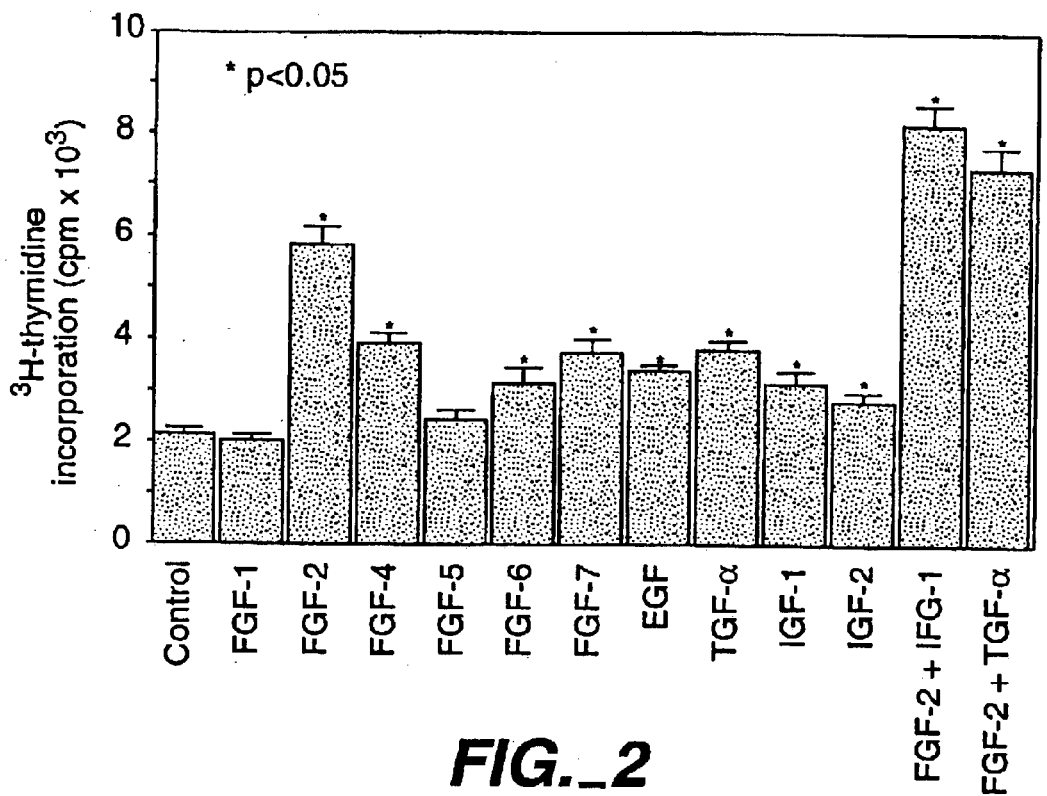
FIG._2
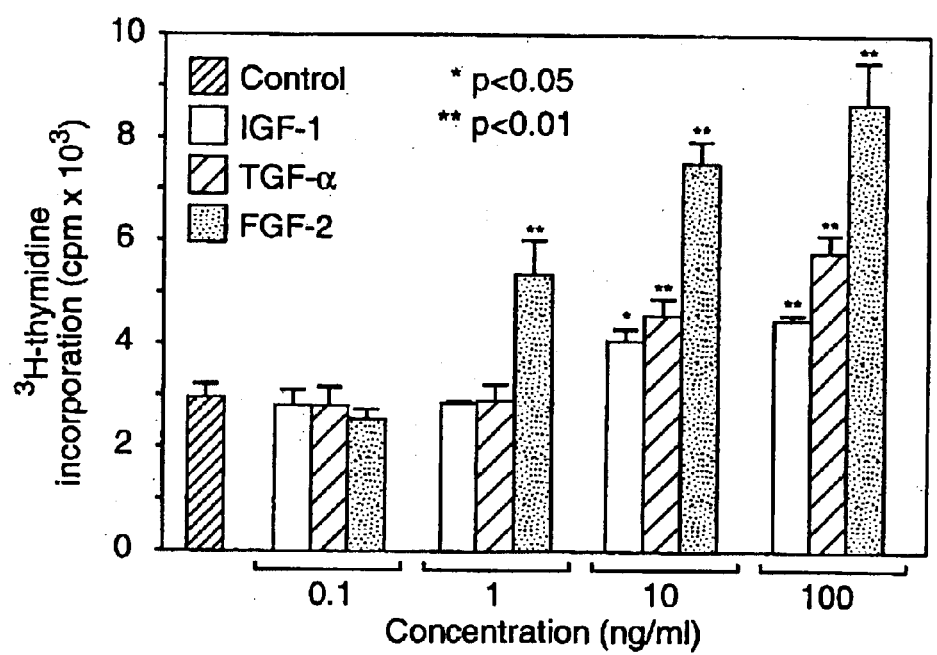
FIG._4

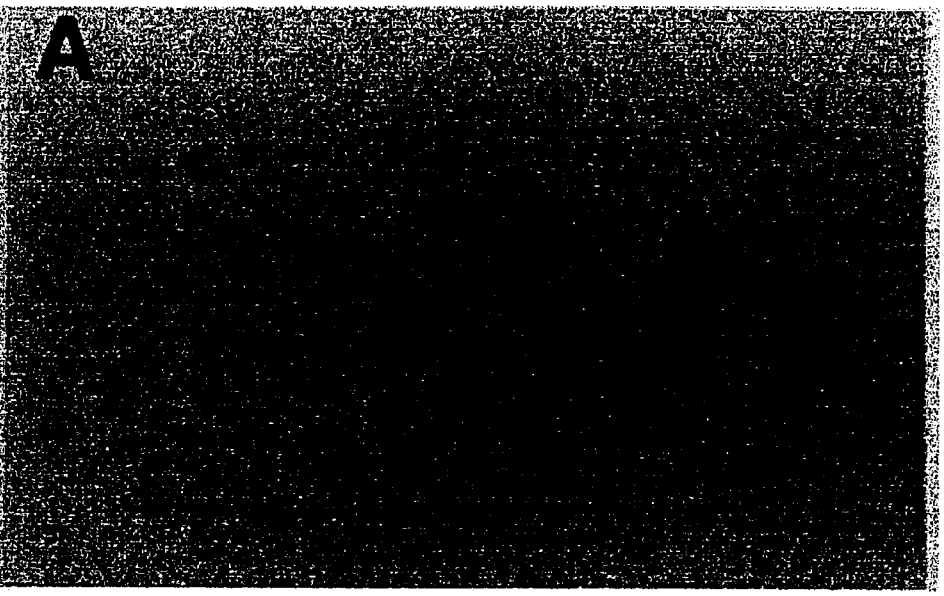
FIG._3A
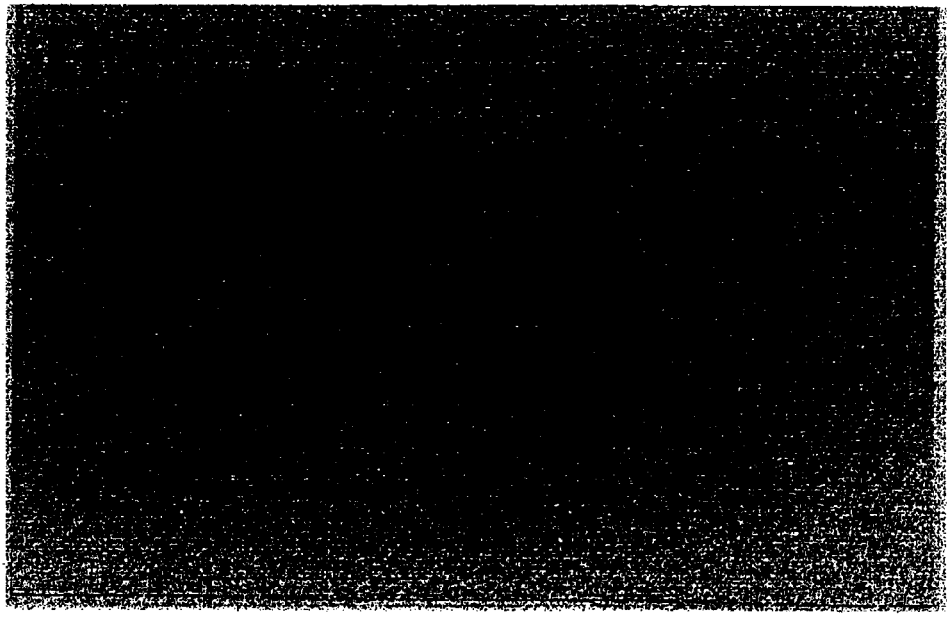
FIG._3B

FIG._5A
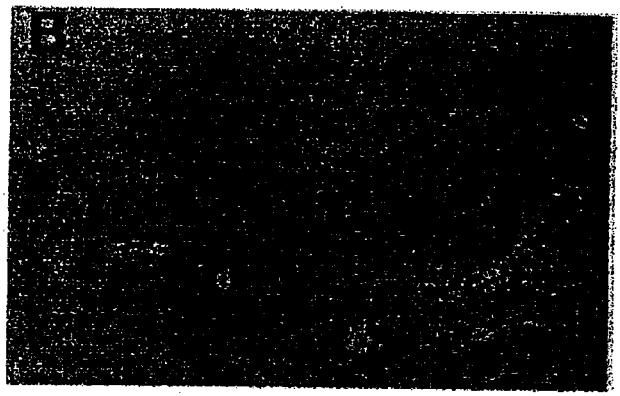
FIG._5B
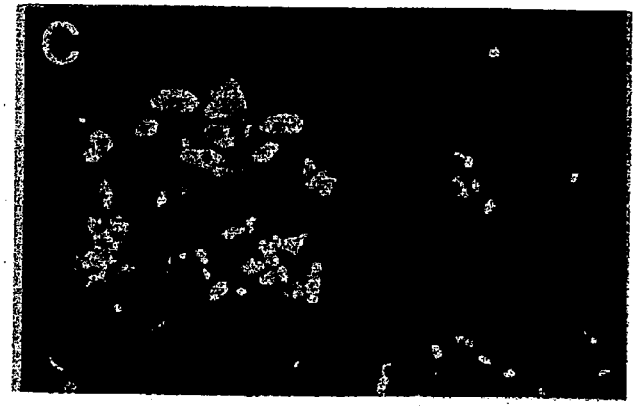
FIG._5C

FIG._5D
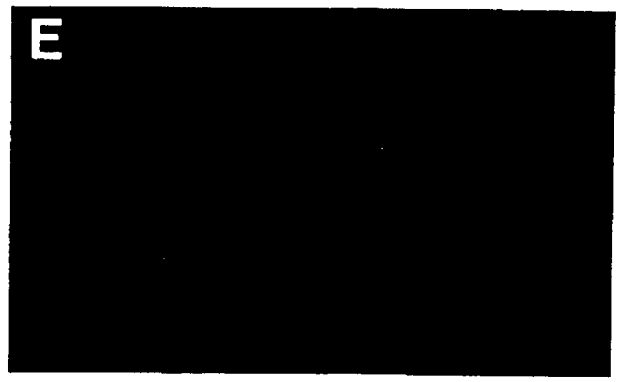
FIG._5E
FIG._5F

FIG._6A
FIG._6B
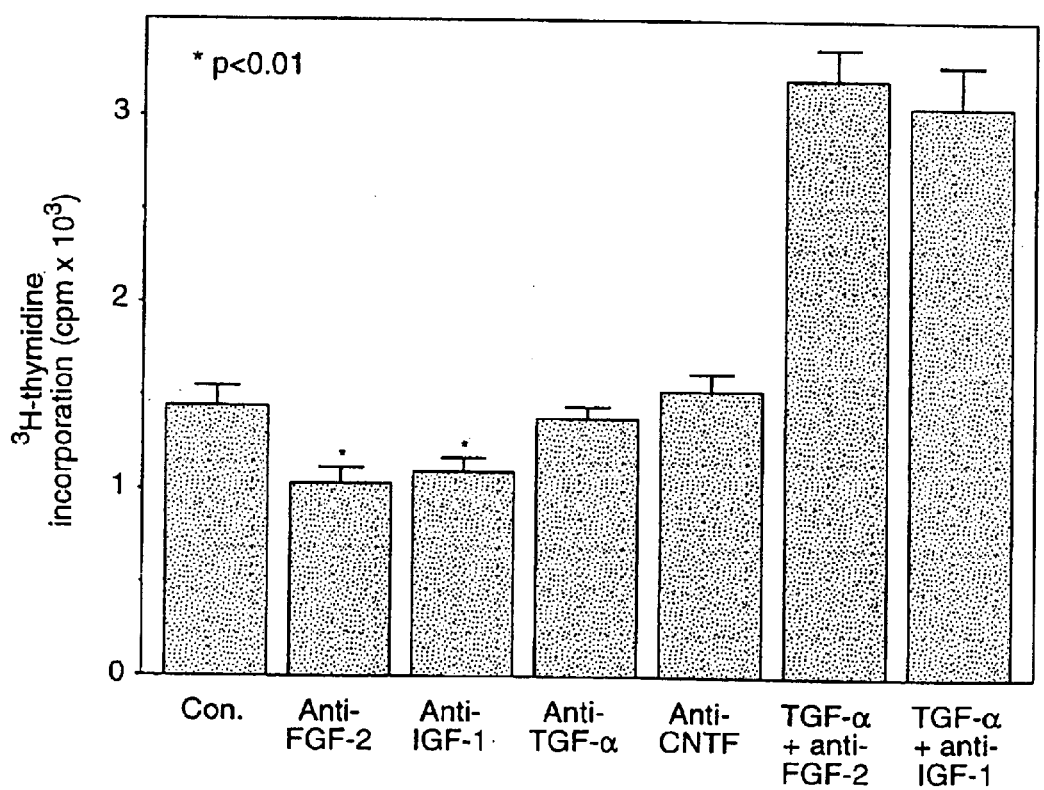
FIG._7

TREATMENT OF INNER EAR HAIR CELLS

This non-provisional application is a continuation of U.S. application Ser. No. 09/644,368, filed on Aug. 23, 2000, now U.S. Pat. No. 6,653,279, which is a divisional of application Ser. No. 08/963,596 filed Oct. 31, 1997 under 37 CFR 1.53(b)(1), now U.S. Pat. No. 6,156,728, and claims priority under 35 U.S.C. § 120 to these applications and under 35 USC Section 119(e) to provisional Application Ser. No. 60/029,538, filed on Nov. 1, 1996, and to provisional Application Ser. No. 60/030,278, filed Nov. 4, 1996, all of which applications are hereby incorporated herein by reference.

BACKGROUND OF THE INVENTION

1. Field of the Invention

This application relates to inducing, promoting, or enhancing the growth, proliferation, or regeneration of inner ear tissue, particularly inner ear epithelial hair cells. In addition, this application provides methods, compositions and devices for prophylactic and therapeutic treatment of inner ear disorders and conditions, particularly hearing impairments. The methods comprise administration of insulin-like growth factor-1 (IGF-1) and/or fibroblast growth factor-2 (FGF-2), or their agonists.

2. Description of Related Disclosures

Hearing impairments are serious handicaps which affect millions of people. Hearing impairments can be attributed to a wide variety of causes, including infections, mechanical injury, loud sounds, aging, and chemical-induced ototoxicity that damages neurons and/or hair cells of the peripheral auditory system. The peripheral auditory system consists of auditory receptors, hair cells in the organ of Corti, and primary auditory neurons, the spiral ganglion neurons in the cochlea. Spiral ganglion neurons ("SGN") are primary afferent auditory neurons that deliver signals from the peripheral auditory receptors, the hair cells in the organ of Corti, to the brain through the cochlear nerve. The eighth nerve connects the primary auditory neurons in the spiral ganglia to the brain stem. The eight nerve also connects vestibular ganglion neurons ("VGN"), which are primary afferent sensory neurons responsible for balance and which deliver signals from the utricle, saccule and ampullae of the inner ear to the brain, to the brainstem. Destruction of primary afferent neurons in the spiral ganglia and hair cells has been attributed as a major cause of hearing impairments. Damage to the peripheral auditory system is responsible for a majority of hearing deficits (Dublin, 1976; Rybak, 1986; Lim, 1986; Pryor, 1994).

Hearing loss or impairment is a common occurrence for mammals. Impairment anywhere along the auditory pathway from the external auditory canal to the central nervous system may result in hearing loss. Auditory apparatus can be divided into the external and middle ear, inner ear and auditory nerve and central auditory pathways. While having some variations from species to species, the general characterization is common for all mammals. Auditory stimuli are mechanically transmitted through the external auditory canal, tympanic membrane, and ossicular chain to the inner ear. The middle ear and mastoid process are normally filled with air. Disorders of the external and middle ear usually produce a conductive hearing loss by interfering with this mechanical transmission. Common causes of a conductive hearing loss include obstruction of the external auditory canal, as can be caused by aural atresia or cerumen; thickening or perforation of the tympanic membrane, as can be caused by trauma or infection; fixation or resorption of the components of the ossicular chain; and obstruction of the Eustachian tube, resulting in a fluid-filled middle-ear space. Auditory information is transduced from a mechanical signal to a neurally conducted electrical impulse by the action of neuro-epithelial cells (hair cells) and SGN in the inner ear. All central fibers of SGN form synapses in the cochlear nucleus of the pontine brain stem. The auditory projections from the cochlear nucleus are bilateral, with major nuclei located in the inferior colliculus, medial geniculate body of the thalamus, and auditory cortex of the temporal lobe. The number of neurons involved in hearing increases dramatically from the cochlea to the auditory brain stem and the auditory cortex. All auditory information is transduced by a limited number of hair cells, which are the sensory receptors of the inner ear, of which the so-called inner hair cells, numbering a comparative few, are critically important, since they form synapses with approximately 90 percent of the primary auditory neurons. By comparison, at the level of the cochlear nucleus, the number of neural elements involved is measured in the hundreds of thousands. Thus, damage to a relatively few cells in the auditory periphery can lead to substantial hearing loss. Hence, many causes of sensorineural loss can be ascribed to lesions in the inner ear. This hearing loss can be progressive. In addition, the hearing becomes significantly less acute because of changes in the anatomy of the ear as the animal ages.

During embryogenesis, the vestibular ganglion, spiral ganglion, and the otic vesicle are derived from the same neurogenic ectoderm, the otic placode. The vestibular and auditory systems thus share many characteristics including peripheral neuronal innervations of hair cells and central projections to the brainstem nuclei. Both of these systems are sensitive to ototoxins that include therapeutic drugs, antineoplastic agents, contaminants in foods or medicines, and environmental and industrial pollutants. Ototoxic drugs include the widely used chemotherapeutic agent cisplatin and its analogs (Fleischman et al., 1975; Stadnicki et al., 1975; Nakai et al., 1982; Berggren et al., 1990; Dublin, 1976; Hood and Berlin, 1986), commonly used aminoglycoside antibiotics, e.g. gentamicin, for the treatment of infections caused by Gram-negative bacteria, (Sera et al., 1987; Hinojosa and Lemer, 1987; Bareggi et al., 1990), quinine and its analogs, salicylate and its analogs, and loop-diuretics.

The toxic effects of these drugs on auditory cells and spiral ganglion neurons are often the limiting factor for their therapeutic usefulness. For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169–71 (1980) or most recent edition). Aminoglycoside antibiotics are generally utilized as broad spectrum antimicrobials effective against, for example, gram-positive, gram-negative and acid-fast bacteria. Susceptible microorganisms include *Escherichia* spp., *Hemophilus* spp., *Listeria* spp., *Pseudomonas* spp., *Nocardia* spp., *Yersinia* spp., *Klebsiella* spp., *Enterobacter* spp., *Salmonella* spp., *Staphylococcus* spp., *Streptococcus* spp., *Mycobacteria* spp., *Shigella* spp., and *Serratia* spp. Nonetheless, the aminoglycosides are used primarily to treat infections caused by gram-negative bacteria and, for instance, in combination with penicillins for the synergistic effects. As implied by the generic name for the family, all the aminoglycoside antibiotics contain aminosugars in glycosidic linkage. Otitis media is a term used to describe infections of the middle ear, which infections are very common, particularly in children. Typically antibiotics are systemically administered for infections of the middle ear, e.g., in a responsive or prophylactic manner. Systemic administration of antibiotics to combat middle ear infection generally results in a prolonged lag time to achieve therapeutic levels in the middle ear, and requires high initial doses in order to achieve such levels. These drawbacks complicate the ability to obtain therapeutic levels and may preclude the use of some antibiotics altogether. Systemic administration is most often effective when the infection has reached advanced stages, but at this point permanent damage may already have been done to the middle and inner ear structure. Clearly, ototoxicity is a dose-limiting side-effect of antibiotic administration. For example, nearly 75% of patients given 2 grams of streptomycin daily for 60 to 120 days displayed some vestibular impairment, whereas at 1 gram per day, the incidence decreased to 25% (U.S. Pat. No. 5,059,591). Auditory impairment was observed: from 4 to 15% of patients receiving 1 gram per day for greater than 1 week develop measurable hearing loss, which slowly becomes worse and can lead to complete permanent deafness if treatment continues.

Ototoxicity is also a serious dose-limiting side-effect for cisplatin, a platinum coordination complex, that has proven effective on a variety of human cancers including testicular, ovarian, bladder, and head and neck cancer. Cisplatin damages auditory and vestibular systems (Fleischman et al., 1975; Stadnicki et al, 1975; Nakai et al., 1982; Carenza et al., 1986; Sera et al., 1987; Bareggi et al., 1990). Salicylates, such as aspirin, are the most commonly used therapeutic drugs for their anti-inflammatory, analgesic, anti-pyretic and anti-thrombotic effects. Unfortunately, they have ototoxic side effects. They often lead to tinnitus ("ringing in the ears") and temporary hearing loss (Myers and Bernstein, 1965). However, if the drug is used at high doses for a prolonged time, the hearing impairment can become persistent and irreversible, as reported clinically (Jarvis, 1966).

Accordingly, there exists a need for means to prevent, reduce or treat the incidence and/or severity of inner ear disorders and hearing impairments involving inner ear tissue, particularly inner ear hair cells, and optionally, the associated auditory nerves. Of particular interest are those conditions arising as an unwanted side-effect of ototoxic therapeutic drugs including cisplatin and its analogs, aminoglycoside-antibiotics, salicylate and its analogs, or loop diuretics. In addition, there exits a need for methods which will allow higher and thus more effective dosing with these ototoxicity-inducing pharmaceutical drugs, while concomitantly preventing or reducing ototoxic effects caused by these drugs. What is needed is a method that provides a safe, effective, and prolonged means for prophylactic or curative treatment of hearing impairments related to inner ear tissue damage, loss, or degeneration, particularly ototoxin-induced and particularly involving inner ear hair cells. The present invention provides compositions and methods to achieve these goals and others as well.

SUMMARY

The present invention is based in part on the discovery disclosed herein that the inner ear hair cells produced FGF-2 in vivo, that utricular epithelial cells expressed FGF receptor in vitro, and that administration of certain growth factors can stimulate the production of new inner hair cells by inducing proliferation of supporting cells which are the hair cell progenitors. Among 30 growth factors examined, FGF-2 was the most potent mitogen. IGF-1 was also effective. Accordingly, it is an object of the invention to provide a means of inducing, promoting, or enhancing the growth, proliferation, or regeneration of inner ear tissue, particularly inner ear epithelial hair cells, in vitro, ex vivo or in vitro. It is a further object of the invention to provide a method for treating a mammal to prevent, reduce, or treat the incidence of or severity of an inner ear hair cell-related hearing impairment or disorder (or balance impairment), particularly an ototoxin-induced or -inducible hearing impairment, by administering to a mammal in need of such treatment a prophylactically or therapeutically effective amount of FGF-2, IGF-1, their agonists, a functional fragment or derivative thereof, a chimeric growth factor comprising FGF-2 or IGF-1, a small molecule or antibody agonist thereof, or a combination of the foregoing. Optionally, a trkB or trkC agonist, preferably a neurotrophin, more preferably NT-4/5, NT-3, or BDNF, and most preferably NT-4/5, or a functional fragment or derivative thereof, a chimeric neurotrophin, a pantropic neurotrophin, or a small molecule or antibody agonist thereof, is also administered in the case where auditory or vestibular neuronal damage is also present or suspected. According to the method of this invention a composition of the invention can be administered at a suitable interval(s) either prior to, subsequent to, or substantially concurrently with the administration of or exposure to hearing-impairment inducing inner ear tissue damage, preferably ototoxin-induced or -inducible hearing impairment.

Also provided are improved compositions and methods for treatments requiring administration of a pharmaceutical having an ototoxic, hearing-impairing side-effect, wherein the improvement includes administering (prophylactically or therapeutically) a therapeutically effective amount of FGF-2, IGF-1, their agonists, a functional fragment or derivative thereof, a chimeric growth factor comprising FGF-2 or IGF-1, a small molecule or antibody agonist thereof, or a combination of the foregoing, to treat or prevent the ototoxicity induced by the pharmaceutical. Accordingly, it is an object of the invention to provide an improved composition containing FGF-2, IGF-1, their agonists, or a combination thereof, in combination with an ototoxic, hearing-impairing pharmaceutical drug for administration to a mammal. Such combination compositions can further contain a pharmaceutically acceptable carrier. The pharmaceutical composition will have lower ototoxicity than the ototoxic pharmaceutical alone, and preferably, will have a higher dosage of the ototoxic pharmaceutical than typically used. Examples of such improved compositions include cisplatin or other ototoxic neoplastic agent or an aminoglycoside antibiotic(s) in combination with FGF-2, IGF-1, their agonists, or a combination thereof. A trkB or trkC agonist is optionally formulated or administered therewith when neuronal damage is present, suspected, or expected.

Still further, the invention relates to the use in medicine of compositions of the invention in cases of bacterial infection. The present invention provides a solution to the art that has long sought a therapy and a medicament which can treat the ototoxic effects currently associated with certain antibiotics, and particularly with the more popular and commonly used aminoglycoside antibiotics without sacrificing the antimicrobial effectiveness of the aminoglycosides.

Still further, the invention relates to the use in medicine of compositions of the invention in cases of cancer. The present invention provides a solution to the art that has long sought a therapy and a medicament which can treat the ototoxic effects currently associated with certain chemotherapeutics, and particularly with the more popular and commonly used cisplatin chemotherapeutics without sacrificing the antineoplastic effectiveness of cisplatin or its analogs.

Still further, the invention relates to the use in medicine of compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use in medicine of compositions of the invention in cases where quinine or quinine-like compounds are needed. The present invention provides a solution to the art that has long sought a therapy and a medicament which can treat the ototoxic effects currently associated with certain quinines without sacrificing their effectiveness.

Additional objects and features of the invention will be apparent to those skilled in the art from the following detailed description and appended claims when taken in conjunction with the figures.

BRIEF DESCRIPTION OF THE DRAWINGS

FIGS. 1A–1G depicts utricular epithelial cell cultures and immunostainings. FIG. 1A shows two intact utricular epithelial sheets separated from P4-5 rats. FIG. 1B shows partially dissociated epithelial sheets at the time of plating. Phase (FIG. 1C) and fluorescence (FIG. 1D) pictures are shown of a 2-day epithelial cell culture labeled with an antibody against vimentin. Immunostaining of the 2-day cultures with an antibody against ZO1 (FIG. 1E), a phalloidin-FITC conjugate (FIG. 1F) and an antibody against pan-cytokeratin (FIG. 1G) are shown. Bar equals 200 $\mu$m for FIGS. 1A and 1B, and 100 $\mu$m for FIGS. 1C–1G.

FIG. 2 is a graph depicting tritiated thymidine incorporation by P4-5 utricular epithelial cells. In each case, an identical volume of suspended cells were plated in 5% fetal bovine serum-supplemented medium in the presence or absence of 100 ng/ml growth factor. $^3$H-thymidine was added 24 hr after plating, and the incorporation was measured 24 hr later. Data collected from 5 or 10 culture wells are expressed as mean±s.e.m. Asterisks indicate a significant increase in the thymidine incorporation compared to the control cultures ($p<0.05$). Relative to cultures containing FGF-2 alone, a combination of FGF-2 with IGF-1 or TGF-$\alpha$ resulted in a significantly higher thymidine incorporation ($p<0.05$).

FIGS. 3A and 3B depict BrdU immunocytochemistry of utricular epithelial cell cultures. FIG. 3A represents a control culture. FIG. 3B represents a culture containing 100 ng/ml of FGF-2. BrdU was added at 24 hours of culture, and the cultures were fixed for immunocytochemistry at 48 hours. Note that the presence of FGF-2 greatly enhanced the number of BrdU-positive cells. Bar equals 200 $\mu$m.

FIG. 4 depicts the dose-dependent mitogenic effects of FGF-2, IGF-1 and TGF-$\alpha$. $^3$H-thymidine incorporation assay was performed in the cultures containing FGF-2, IGF-1 and TGF-$\alpha$ at concentrations ranging from 0.1 to 100 ng/ml and in the control cultures, as described in the Examples. The symbols * and ** indicate $p<0.05$ and $p<0.01$ as compared to the control cultures, respectively. Relative to IGF-1 and TGF-$\alpha$, FGF-2 was more potent at concentrations ranging from 1–100 ng/ml ($p<001$).

FIGS. 5A–5F depict immunocytochemistry of the utricular epithelial cell cultures with antibodies against receptors for FGF, IGF-1 and NGF. Shown are fluorescence (FIGS. 5A, 5C, 5E) and phase (FIGS. 5B, 5D, 5F) pictures of the 2-day epithelial cell cultures with antibodies against FGF receptor (FIGS. 5A, 5B), against IGF-1 receptor b (FIGS. 5C, 5D) and against TrkA, a high-affinity binding receptor for NGF (FIGS. 5E, 5F). Note that while many of the cultured cells express high levels of FGF receptor and IGF-1 receptor, no detectable TrkA receptor was observed. Bar equals 100 $\mu$m.

FIGS 6A and 6B depict fluorescence (FIG. 6A) and phase (FIG. 6B) microscopy of immunohistochemistry of P5 rat utricular sections with a monoclonal antibody against FGF-2. Note that while hair cells were clearly labeled by the FGF-2 antibody in the sensory epithelium, the supporting cells which are located underneath and surrounding hair cells and basilar membrane cells were not labeled (FIG. 6A). Abbreviations: HC, hair cells; SC, supporting cells; SE, sensory epithelium; BM, basilar membrane area containing basilar membrane and underneath connective tissue. Bar equals 50 $\mu$m.

FIG. 7 is a graph depicting inhibition of tritiated thymidine incorporation of P4-5 utricular epithelial cells by anti-FGF-2 or anti-IGF-1 neutralizing antibodies. In each case, an identical volume of suspended cells was plated in 1% fetal bovine serum-supplemented medium in the presence or absence of anti-FGF-2, anti-IGF-1, anti-TGF-$\alpha$, or anti-CNTF antibodies or a combination of TGF-$\alpha$ (100 ng/ml) and anti-FGF-2 antibody or TGF-$\alpha$ (100 ng/ml) and anti-IGF-1 antibody. $^3$H-thymidine was added 24 hr after plating and the incorporation was measured 24 hr later. Data collected from 10 culture wells are expressed as mean±s.e.m. Note that anti-FGF-2 and anti-IGF-1 antibodies, but not anti-TGF-$\alpha$ and anti-CNTF antibodies, exhibited a significant inhibition. The mitogenic effect of TGF-$\alpha$ was not influenced by the presence of anti-FGF-2 antibody or anti-IGF-1 antibody.

DETAILED DESCRIPTION OF THE PREFERRED EMBODIMENTS

Definitions

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human.

As used herein, "IGF-1" refers to insulin-like growth factor from any species, including bovine, ovine, porcine, equine, and preferably human, in native-sequence or in variant form, and from any source, whether natural, synthetic, or recombinant. Preferred herein for animal use is that form of IGF-1 from the particular species being treated, such as porcine IGF-1 to treat pigs, ovine IGF-1 to treat sheep, bovine IGF-1 to treat cattle, etc. Preferred herein for human use is human native-sequence, mature IGF-1, more preferably without a N-terminal methionine, prepared, for example, by the process described in EP 230,869 published Aug. 5, 1987; EP 128,733 published Dec. 19, 1984; or EP 288,451 published Oct. 26, 1988. Additional preferred IGF-1 variants are those described in U.S. Pat. Nos. 5,077,276; 5,164,370; or 5,470,828; or in WO 87/01038, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-1, des(1-3)-IGF-1, or des-IGF-1).

Native-sequence IGF-1 is recombinantly produced and is available from Genentech, Inc., South San Francisco, Calif., for clinical investigations.

As used herein, "FGF-2" refers to fibroblast growth factor-2 from any species, including bovine, ovine, porcine; equine, and preferably human, in native-sequence or in variant form, and from any source, whether natural, synthetic, or recombinant. Preferred herein for animal use is that form of FGF-2 from the particular species being treated, such as porcine FGF-2 to treat pigs, ovine FGF-2 to treat sheep, bovine FGF-2 to treat cattle, etc. Preferred herein for human use is human native-sequence, mature FGF-2. U.S. Pat. No. 5,352,589, provides suitable deletion mutants of FGF-2 and production thereof. U.S. Pat. No. 5,514,566, provides methods of producing recombinant FGF-2. U.S. Pat. No. 5,464,943, provides DNA encoding glycosylated FGF-2 and methods for production thereof. Methods for producing FGFs using genetic engineering techniques are known. The production methods using the genetic engineering techniques are reported in *Biochem. Biophys. Res. Commun.* 146:470 (1987); *Biotechnology*, 5:960 (1987); *J. Biol. Chem.* 263:16471 (1988); *J. Biol. Chem.* 263:18452 (1988); *J. Biol. Chem.* 263:16297 (1988), and the like.

"Treatment" refers to both therapeutic treatment and prophylactic or preventative measures, wherein the object is to prevent or slow down (lessen) inner ear tissue-damage-related hearing disorder or impairment (or balance impairment), preferably ototoxin-induced or inducible, and involving inner ear hair cells. Those in need of treatment include those already experiencing a hearing impairment, those prone to having the impairment, and those in which the impairments are to be prevented. The hearing impairments are due to inner ear hair cell damage or loss, wherein the damage or loss is caused by infections, mechanical injury, loud sounds, aging, or, preferably, chemical-induced ototoxicity, wherein ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxic agent" in the context of the present invention is meant a substance that through its chemical action injures, impairs or inhibits the activity of a component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin, taxol, or dideoxy-compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillin or chloramphenicol, or megadoses of vitamins A, D, or B6, salicylates, quinines and loop diuretics. Other toxic agents that can cause ototoxicity-inducing hearing impairment can be identified and characterized by methods as taught herein. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

As used herein "chronic" refers to a disorder that is not acute but rather occurs more or less on a continuous level. A "disorder" is any condition that would benefit from treatment with the factors and compositions of the invention. The disorder being treated may be a combination of two or more of the above disorders, and may include auditory or vestibular neuron damage or loss.

MODES FOR CARRYING OUT THE INVENTION

The patients targeted for treatment by the current invention include those patients with inner ear hair cell related conditions as defined herein.

Hearing impairments relevant to the invention are preferably sensory hearing loss due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than 85 decibels (db) that damages the inner ear. Hearing loss includes presbycusis, which is a sensorineural hearing loss occurring as a normal part of aging, fractures of the temporal bone extending into the middle ear and rupturing the tympanic membrane and possibly the ossicular chain, fractures affecting the cochlea, and acoustic neurinoma, which are tumors generally of Schwann cell origin that arise from either the auditory or vestibular divisions of the 8th nerve. Preferably, the hearing loss is caused by an ototoxic drug that effects the auditory portion of the inner ear, particularly inner ear hair cells. Incorporated herein by reference are Chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Tests are known and available for diagnosing hearing impairments. Neuro-otological, neuro-ophthalmological, neurological examinations, and electro-oculography can be used. (Wennmo et al. *Acta Otolaryngol* (1982) 94:507–15). Sensitive and specific measures are available to identify patients with auditory impairments. For example, tuning fork tests can be used to differentiate a conductive from a sensorineural hearing loss and determine whether the loss is unilateral. An audiometer is used to quantitate hearing loss, measured in decibels. With this device the hearing for each ear is measured, typically from 125 to 8000 Hz, and plotted as an audiogram. Speech audiometry can also be performed.

The speech recognition threshold, the intensity at which speech is recognized as a meaningful symbol, can be determined at various speech frequencies. Speech or phoneme discrimination can also be determined and used an indicator of sensorineural hearing loss since analysis of speech sounds relies upon the inner ear and 8th nerve. Tympanometry can be used to diagnose conductive hearing loss and aid in the diagnosis of those patients with sensorineural hearing loss. Electrocochleography, measuring the cochlear microphonic response and action potential of the 8th nerve, and evoked response audiometry, measuring evoked response from the brainstem and auditory cortex, to acoustic stimuli can be used in patients, particularly infants and children or patients with sensorineural hearing loss of obscure etiology. These tests serve a diagnostic function as well as a clinical function in assessing response to therapy.

Sensory and neural hearing losses can be distinguished based on tests for recruitment (an abnormal increase in the perception of loudness or the ability to hear loud sounds normally despite a hearing loss), sensitivity to small increments in intensity, and pathologic adaptation, including stapedial reflex decay. Recruitment is generally absent in neural hearing loss. In sensory hearing loss the sensation of loudness in the affected ear increases more with each increment in intensity than it does in the normal ear. Sensitivity to small increments in intensity can be demonstrated by presenting a continuous tone of 20 db above the hearing threshold and increasing the intensity by 1 db briefly and intermittently. The percentage of small increments detected yields the "short increment sensitivity index" value. High values, 80 to 100%, is characteristic of sensory hearing loss, whereas a neural lesion paiient and those with normal hearing cannot detect such small changes in intensity. Pathologic adaptation is demonstrated when a patient cannot continue to perceive a constant tone above the threshold of hearing; also known as tone decay. A Bekesy automatic audiometer or equivalent can be used to determine these clinical and diagnostic signs; audiogram patterns of the Type II pattern, Type III pattern and Type IV pattern are indicative of preferred hearing losses suitable for the treatment methods of the invention. As hearing loss can often be accompanied by vestibular impairment, vestibular function can be tested, particular when presented with a sensorineural hearing loss of unknown etiology. When possible diagnostics for hearing loss, such as audiometric tests, should be performed prior to exposure in order to obtain a patient normal hearing baseline. Upon exposure, particularly to an ototoxic drug, audiometric tests should be performed twice a week and continued testing should be done even after cessation of the drug treatment since hearing loss may not occur until several days after cessation. U.S. Pat. No. 5,546,956, provides methods for testing hearing that can be used to diagnose the patient and monitor treatment. U.S. Pat. No. 4,637,402, provides a method, for quantitatively measuring a hearing defect, that can be used to diagnose the patient and monitor treatment.

Studies in lower vertebrates and avian systems indicate that supporting cells in the inner ears are hair cell progenitors (see for example, 27 and 49). In response to injury supporting cells are induced to proliferate and differentiate into new hair cells. However, in the mammalian system, supporting cell proliferation and hair cell regenerating occurs at a much lower frequency than in the avian system (48, 92, 127). The mammalian utricular epithelial supporting cells express epithelial antigens, including the right junction protein (ZO1), cytokeratin, and F-actin, but not fibroblast antigens, vimentin and Thy1.1, or glial cell and neuronal antigens. Characteristically, in culture, supporting cells require cell-to-cell contact for survival, which can be provided by other supporting cells, and by a fibroblast monolayer as observed with dissociated chick cochlear epithelial cells (16). Identification of the molecular and cellular mechanisms underlying the development and regeneration of hair cells, has been hampered by the small tissue size, the complicated bony structures of the inner ear, and by the lack of hair cell progenitor culture systems.

The utricular epithelium is composed of a central, sensory epithelium and a peripheral, marginal zone (Lambert 1994). The results obtained herein reflect primarily the proliferation of sensory epithelial cells, since in the examples in which utricular cells were cultured, either only minimal carryover of and proliferation by transitional cells located at the sensory-marginal zone border may have occurred in some examples, or the sensory epithelium has been obtained completely free of the peripheral non-sensory epithelial cells in other examples. In addition, the in vivo analysis presented herein are consistent with the in vitro results.

In one embodiment the invention constitutes a method for treating a mammal having or prone to a hearing (or balance) impairment or treating a mammal prophylactically to prevent or reduce the occurrence or severity of a hearing (or balance) impairment that would result from inner ear cell injury, loss, or degeneration, preferably caused by an ototoxic agent, wherein a therapeutically effective amount of a inner ear supporting cell growth factor or agonist of the invention, which are compounds that promote hair cell regeneration, growth, proliferation, or prevent or reduce cytotoxicity of hair cells by induction of the proliferation of supporting epithelial cells leading to generation of new hair cells. Such molecules are agonists of the utricular epithelial cell FGF- and IGF-1-high-affinity binding receptors that were identified herein as expressed on the surface of sensory epithelium cells. Preferred compounds are FGF-2, IGF-1, agonists thereof, a functional fragment or derivative thereof, a chimeric growth factor comprising FGF-2 or IGF-1, such as those containing the receptor-binding sequences from FGF-2 or IGF-1, a small molecule mimic of IGF-1 or FGF-2, an antibody agonist thereof, or a combination of the foregoing. Optionally, a trkB or trkC agonist is also administered to the mammal when neuronal cell damage is also suspected or expected. Preferably the trkB or trkC agonist is a neurotrophin, more preferably neurotrophin NT-4/5, NT-3, or BDNF, a functional fragment, fusion or derivative thereof, such as a chimeric neurotrophin (having both trkB and trkC agonism), a pantropic neurotrophin, or a small molecule or antibody agonist thereof, as discussed in detail herein. Most preferably the agonist is NT-4/5 or a chimeric or pantropic variant thereof having at least both trkB and trkC agonist activity. A preferred chimeric or pantropic neurotrophin has a region conferring NT-3-receptor binding specificity and a region conferring NT-4/5-receptor binding specificity. A preferred pantropic neurotrophin is MNTS-1. In a preferred embodiment the binding of a chimeric or pantropic neurotrophin to a neurotrophic receptor is at least 80% of the binding of the natural neurotrophin ligand to the receptor. When the patient is human, the growth factors and neurotrophins are preferably human growth factors and neurotrophins or derived from human gene sequences, in part to avoid or minimize recognition of the agonist as foreign. The methods of the invention are particularly effective when the hearing impairment is ototoxin induced or inducible.

It is another object of the invention to provide a method for treating a mammal to prevent, reduce, or treat a hearing impairment, disorder or imbalance, preferably an ototoxin-induced hearing condition, by administering to a mammal in need of such treatment a composition of the invention. One embodiment is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

The methods of the invention are particularly effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2.

Hearing impairments induced by aminoglycosides can be prevented or reduced by the methods of the invention. Although the aminoglycosides are particularly useful due to their rapid bactericidal action in infections by susceptible organisms, their use is limited to more severe, complicated infections because of ototoxic and nephrotoxic side-effects. For this reason the aminoglycosides are considered to have a low therapeutic/risk ratio compared to other antibiotics used systemically.

Aminoglycosides are a class of compounds characterized by the ability to interfere with protein synthesis in microorganisms. Aminoglycosides consist of two or more amino sugars joined in a glycoside linkage to a hexose (or aminocyclitol)nucleus. The hexose nuclei thus far known are either streptidine or 2-deoxystreptamine, though others may be anticipated. Aminoglycoside families are distinguished by the amino sugar attached to the aminocyclitol. For example, the neomycin family comprises three amino sugars attached to the central 2-deoxystreptamine. The kanamycin and glutamicin families have only two aminosugars attached to the aminocyclitol. Aminoglycosides include: neomycins (e.g. neomycin B and analogs and derivatives thereof), paromomycin, ribostamycin, lividomycin, kanamycins (e.g. kanamycin A, kanamycin B, and analogs and derivatives thereof), amikacin, tobramycin, viomycin, gentamicin (e.g., gentamicin C1, gentamicin C1a, gentamicin C2, and analogs and derivatives thereof), sisomicin, netilmicin, streptomycin, dibekacin, fortimicin, and dihydrostreptomycin.

The aminoglycoside antibiotic which can be employed in conjunction with the ototoxicity inhibiting compositions of the invention is any aminoglycoside antibiotic. Examples of such aminoglycoside antibiotics include kanamycin (Merck Index 9th ed. #5132), gentamicin (Merck Index 9th ed. #4224), amikacin (Merck Index 9th ed. #A1), dibekacin (Merck Index 9th ed. #2969), tobramycin (Merck Index 9th ed. #9193), streptomycin (Merck Index 9th ed. #8611/8612), paromomycin (Merck Index 9th ed. #6844), sisomicin (Merck Index 9th ed. #8292), isepamicin and netilmicin, all known in the art. The useful antibiotics include the several structural variants of the above compounds (e.g. kanamycin A, B and C; gentamicin A, C1, C1a, C2 and D; neomycin B and C and the like). The free bases, as well as pharmaceutically acceptable acid addition salts of these aminoglycoside antibiotics, can be employed.

For the purpose of this disclosure, the terms "pharmaceutically acceptable acid addition salt" shall mean a mono or poly salt formed by the interaction of one molecule of the aminoglycoside antibiotic with one or more moles of a pharmaceutically acceptable acid. Included among those acids are acetic, hydrochloric, sulfuric, maleic, phosphoric, nitric, hydrobromic, ascorbic, malic and citric acid, and those other acids commonly used to make salts of amine-containing pharmaceuticals.

Accordingly, the methods and compositions of the invention find use for the prevention and treatment of opportunistic infections in animals and man which are immunosuppressed as a result of either congenital or acquired immunodeficiency or as a side-effect of chemotherapeutic treatment. According in an alternate embodiment of the present invention, a composition of the invention is used advantageously in combination with a known antimicrobial agent to provide improved methods and compositions to prevent and/or treat diseases induced by gram positive bacteria including, but not limited to: *Staphylococcus aureus, Streptococcus pneumonia, Hemophilus influenza*; gram negative bacteria including, but not limited to: *Escherichia coli; Bacterium enteritis, Francisella tularensis*; acid-fast bacteria including, but not limited to *Mycobacterium tuberculosis*, and *Mycobacterium leprae*. Use of a combination of an antimicrobial agent together with a composition of the invention is advantageous with antibacterial aminoglycosides such as gentamicin, streptomycin, and the like which are known to have serious ototoxicity, which reduce the usefulness of such antimicrobial agents. Use of a composition of the invention in combination with such agents permits a lower dosage of the toxic antimicrobial agents while still achieving therapeutic (antibacterial) effectiveness.

In some embodiments the composition of the invention is co-administered with an ototoxin. For example, an improved method is provided for treatment of infection of a mammal by administration of an aminoglycoside antibiotic, the improvement comprising administering a therapeutically effective amount of FGF-2, IGF-1 or an agonist thereof, to the patient in need of such treatment to reduce or prevent ototoxin-induced hearing impairment associated with the antibiotic. In yet another embodiment is provided an improved method for treatment of cancer in a mammal by administration of a chemotherapeutic compound, the improvement comprises administering a therapeutically effective amount of a composition of the invention to the patient in need of such treatment to reduce or prevent ototoxin-induced hearing impairment associated with the chemotherapeutic drug.

Also provided herein are methods for promoting new inner ear hair cells by inducing inner ear supporting cell proliferation regeneration, or growth upon, prior to, or after exposure to an agent or effect that is capable of inducing a hearing or balance impairment or disorder. Such agents and effects are those described herein. The method includes the step of administering to the inner ear hair cell an effective amount of FGF-2, IGF-1, or agonist thereof, or factor disclosed herein as useful. Preferably, the method is used upon, prior to, or after exposure to a hearing-impairing ototoxin.

In one embodiment the methods of treatment are applied to hearing impairments resulting from the administration of a chemotherapeutic agent to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas.

In one embodiment the methods of the invention are applied to hearing impairments resulting from the administration of quinine and its synthetic substitutes, typically used in the treatment of malaria, to treat its ototoxic side-effect.

In another embodiment the methods of the invention are applied to hearing impairments resulting from administration of a diuretic to treat its ototoxic side-effect. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in nonedematous states such as hypertension, hypercalcemia, idiopathic hypercalciuria, and nephrogenic diabetes insipidus.

In another embodiment the compositions of the invention are administered with an agent that promotes neuronal cell growth, proliferation, or regeneration. As known in the art, low concentrations of gentamicin preferentially kills hair cells while the damage to the ganglion neurons is not significant. However, high concentrations of gentamicin induce degeneration of ganglion neurons as well as hair cells. Accordingly, this dual toxicity of aminoglycosides can be treated by the methods of the invention, preferably with compositions of the invention.

The FGF-2 and/or IGF-1, or agonist, is directly administered to the patient by any suitable technique, including parenterally, intranasally, intrapulmonary, orally, or by absorption through the skin. If they are administered together, they need not be administered by the same route. They can be administered locally or systemically. Examples of parenteral administration include subcutaneous, intramuscular, intravenous, intraarterial, and intraperitoneal, and intracochlear administration. They can be administered by daily subcutaneous injection. They can be administered by implants. They can be administered in liquid drops to the ear canal, delivered to the scala tympani chamber of the inner ear, or provided as a diffusible member of a cochlear hearing implant.

The IGF-1 and FGF-2, or agonist, can be combined and directly administered to the mammal by any suitable technique, including infusion and injection. The specific route of administration will depend, e.g., on the medical history of the patient, including any perceived or anticipated side effects using FGF-2 or IGF-1 alone, and the particular disorder to be corrected. Examples of parenteral administration include subcutaneous, intramuscular, intravenous, intraarterial, and intraperitoneal administration. Most preferably, the administration is by continuous infusion (using, e.g., slow-release devices or minipumps such as osmotic pumps or skin patches), or by injection (using, e.g., intravenous or subcutaneous means). The administration may also be as a single bolus or by slow-release depot formulation. The agonist(s) is administered in an acute or chronic fashion, as may be required, for prophylactic and therapeutic applications, by a number of routes including: injection or infusion by intravenous, intraperitoneal, intracerebral, intramuscular, intradermally, intraocular, intraarterial, subcutaneously, or intralesional routes, topical administration, orally if an orally active small molecule is employed, using sustained-release systems as noted below, or by an indwelling catheter using a continuous administration means such as a pump, by patch, or implant systems, e.g., implantation of a sustained-release vehicle or immuno-isolated cells secreting the growth factor(s) and/or neurotrophin(s). Agonist(s) is administered continuously by infusion or by periodic bolus injection if the clearance rate is sufficiently slow, or by administration into the blood stream, lymph, CNS or spinal fluid. A preferred administration mode is directly to the affected portion of the ear or vestibule, topically as by implant for example, and, preferably to the affected hair cells, their supporting cells, and (optionally to) associated neurons, so as to direct the molecule to the source and minimize side,effects of the agonists.

As noted the compositions can be injected through chronically implanted cannulas or chronically infused with the help of osmotic minipumps. Subcutaneous pumps are available that deliver proteins through a small tubing to the appropriate area. Highly sophisticated pumps can be refilled through the skin and their delivery rate can be set without surgical intervention. Examples of suitable administration protocols and delivery systems involving a subcutaneous pump device or continuous infusion through a totally implanted drug delivery system are those used for the administration of dopamine, dopamine agonists, and cholinergic agonists to Alzheimer patients and animal models for Parkinson's disease described by Harbaugh, *J. Neural Transm. Suppl.*, 24: 271–277 (1987) and DeYebenes et al., *Mov. Disord.*, 2: 143–158 (1987), the disclosures of which are incorporated herein by reference. It is envisioned that it may be possible to introduce cells actively producing agonist into areas in need of increased concentrations of agonist.

An effective amount of agonist(s) to be employed therapeutically will depend, for example, upon the therapeutic objectives, the route of administration, the species of the patient, and the condition of the patient. Accordingly, it will be necessary for the therapist to titer the dosage and modify the route of administration as required to obtain the optimal therapeutic effect. As is known in the art, adjustments for age as well as the body weight, general health, sex, diet, time of administration, drug interaction and the severity of the disease may be necessary, and will be ascertainable with routine experimentation by those skilled in the art. A typical daily dosage of agonists used alone might range from about 1 $\mu$g/kg to up to 100 mg/kg of patient body weight or more per day, depending on the factors mentioned above, preferably about 10 $\mu$g/kg/day to 10 mg/kg/day. Typically, the clinician will administer agonist until a dosage is reached that repairs, maintains, and, optimally, reestablishes neuron function to relieve the hearing impairment. Generally, the agonist is formulated and delivered to the target site and a dosage capable of establishing at the site an agonist level greater than about 0.1 ng/ml, more typically from about 0.1 ng/ml to 5 mg/ml, preferably from about 1 to 2000 ng/ml. In a specific embodiment of the invention, an effective pharmaceutical composition, may provide a local concentration of between about 1 and 100 ng/ml, preferably 5 to 25 ng/ml, and more preferably, between 10 and 20 ng/ml. The progress of this therapy is easily monitored by conventional assays and hearing or balance diagnostic methods.

If two agonists are administered together, they need not be administered by the same route, nor in the same formulation. However, they can be combined into one formulation as desired. In a preferred embodiment FGF-2 optionally is combined with or administered in concert with IGF-1. Both agonists can be administered to the patient, each in effective amounts or each in amounts that are sub-optimal but when combined are effective. Preferably such amounts are about 10 $\mu$g/kg/day to 10 mg/kg/day, preferably 100 to 200 $\mu$g/kg/day, of each. In another preferred embodiment the administration of both agonists is topically by injection using, e.g., means to access the inner ear, depending on the type of agonist employed. More preferably the administration is by implant or patch. Typically, the clinician will administer the agonist(s) until a dosage is reached that achieves the desired effect for treatment of the hearing impairment. The progress of this therapy is easily monitored by conventional assays.

The FGF-2 and/or IGF-1 to be used in the therapy will be formulated and dosed in a fashion consistent with good medical practice, taking into account the clinical condition of the individual patient (especially the side effects of treatment with FGF-2 or IGF-1 alone), the site of delivery of the IGF-1 and FGF-2 composition(s), the method of administration, the scheduling of administration, and other factors known to practitioners. The "effective amounts" of each component for purposes herein are thus determined by such considerations and are amounts that prevent damage or degeneration of inner ear cell function or restore inner ear cell function.

The FGF-2 may also be administered so as to have a continual presence in the inner ear that is maintained for the duration of the administration of the FGF-2. This is most preferably accomplished by means of continuous infusion via, e.g., mini-pump such as an osmotic mini-pump. Alternatively, it is properly accomplished by use of frequent injections or topical administration of FGF-2 (i e., more than once daily, for example, twice or three times daily).

In yet another embodiment, FGF-2 may be administered using long-acting FGF-2 formulations that either delay the clearance of FGF-2 from the inner ear or cause a slow release of FGF-2 from, e.g., an injection or administration site. The long-acting formulation that prolongs FGF-2 plasma clearance may be in the form of FGF-2 complexed, or covalently conjugated (by reversible or irreversible bonding) to a macromolecule such as a water-soluble polymer selected from PEG and polypropylene glycol homopolymers and polyoxyethylene polyols, i.e., those that are soluble in water at room temperature. Alternatively, the FGF-2 may be complexed or bound to a polymer to increase its circulatory half-life. Examples of polyethylenepolyols and polyoxyethylenepolyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides. The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1–C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

In another embodiment, the patients identified above are treated with an effective amount of IGF-1. As a general proposition, the total pharmaceutically effective amount of IGF-1 administered parenterally per dose will be in the range of about 10 µg/kg/day to 10 mg/kg/day, preferably 100 to 200 µg/kg/day, of patient body weight, although, as noted above, this will be subject to a great deal of therapeutic discretion.

The IGF-1 may be administered by any means, as noted for FGF-2 or their combination, including injections or infusions. As with the FGF-2, the IGF-1 may be formulated so as to have a continual presence in the inner ear during the course of treatment, as described above for FGF-2. Thus, it may be covalently attached to a polymer, made into a sustained-release formulation, or provided by implanted cells producing the factor.

In addition, the IGF-1 is appropriately administered together with any one or more of its binding proteins, for example, those currently known, i.e., IGFBP-1, IGFBP-2, IGFBP-3, IGFBP-4, IGFBP-5, or IGFBP-6. The IGF-1 may also be coupled to a receptor or antibody or antibody fragment for administration. The preferred binding protein for IGF-1 herein is IGFBP-3, which is described in U.S. Pat. No. 5,258,287 and by Martin et al., *J. Biol. Chem.*, 261:8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-1 may be accomplished, for example, by the methods described in U.S. Pat. Nos. 5,187,151 and 5,407,913. Briefly, the IGF-1 and IGFBP are administered in effective amounts by in a molar ratio of from about 0.5:1 to about 3:1. Nearly all IGF-1 in blood is bound to IGFBP-3, and IGF/IGFBP-3 normally circulates in the form of a complex in humans and other mammals. This complex associates with a third protein (ALS), which is present in excess over the normal concentrations of IGF and IGFBP-3. Therefore, ALS is found both associated with the IGF/IGFBP-3 complex and in the free form. The resultant ternary complex has a size of about 150 kD. Administration of the complex of IGF and IGFBP-3, either obtained from natural or recombinant sources, results in the formation of the ternary complex with the normally excess ALS. This type of treatment appears to produce a long term increase in the level of circulating IGF, which is gradually released from the ternary or binary complex. This mode of administration avoids the detrimental side effects associated with administration of free IGF-1 (e.g., hypoglycemia, suppression of growth hormone and ALS production, and release of endogenous IGF-II from endogenous IGFBP-3 since administered free IGF-1 replaces endogenous IGF-II in normally circulating IGF-II/IGFBP-3 complexes). IGFBP-4 and IGFBP-6 are glycosylated proteins which are widely distributed in the body. The primary structure of IGFBP-4 was reported by Shimasaki et al. (*Mol. Endocrinol.* (1990) 4:1451–1458). IGFBP-6, whose cDNA has been isolated by Shimasaki et al. (*Mol. Endocrinol.* (1991) 4:938–48), has a much greater affinity for IGF-II than for IGF-1. IGFBP-5 is a 252 amino acid binding protein which is not glycosylated. Shimasaki et al. (*J. Biol. Chem.* (1991)266:10646–53) cloned human IGFBP-5 cDNA from a human placenta library.

Depending on the binding, metabolic and pharmacokinetic characteristics required in the IGF/IGFBP complex formulation,these binding proteins can be added to the complex formulation in various proportions. These IGFBP's can be combined in a wide variety of ratios with IGF-1 and/or IGF-II. Because IGF and IGFBP-3 naturally complex in a 1:1 molar ratio, a composition of equimolar amounts of IGF and IGFBP-3 is preferred, as noted above. The product can be formulated with IGF:IGFBP-3 molar ratios ranging from 0.5 to 1.5. More preferably, the molar ratio is 0.9 to 1.3; and most preferably, the product is formulated with approximately a 1:1 molar ratio. When other IGFBP(s) are used, the ratio of IGFBP(s) to IGF can vary. IGF and IGFBP are preferably human proteins obtained from natural or recombinant sources. Most preferably, IGF and IGFBP are human IGF-1 and IGFBP-3 made by recombinant means and designated rhIGF-1 and rhIGFBP-3, respectively. rhIGFBP-3 can be administered in glycosylated or non-glycosylated form. *E. coli* is a source of the recombinant non-glycosylated IGFBP-3. Glycosylated IGFBP-3 can be obtained in recombinant form from Chinese hamster ovary (CHO) cells.

It is noted that practitioners devising doses of both IGF-1 and FGF-2 should take into account known side effects of treatment with these factors. The major apparent side effect of IGF-1 is hypoglycemia. Guler et al., *Proc. Natl. Acad. Sci. USA*, 86:2868–2872 (1989).

IGF-1 concentrations can be measured in samples using RIA or ELISA following acid ethanol extraction (IGF-1 RIA Kit, Nichols Institute. San Juan Capistrano, Calif.). FGF-2 can be measured similarly or with other suitably sensitive and specific means.

Delivery of therapeutic agents in a controlled and effective manner with respect to tissue structures of the inner ear, e.g., those portions of the ear contained within the temporal bone which is the most dense bone tissue in the entire human body, is known. Exemplary inner ear tissue structures of primary importance include but are not limited to the cochlea, the endolymphatic sac/duct, the vestibular labyrinth, and all of the compartments which include these components. Access to the foregoing inner ear tissue regions is typically achieved through a variety of structures, including but not limited to the round window membrane, the oval window/stapes foot plate, and the annular ligament. The middle ear can be defined as the physiological air-containing tissue zone behind the tympanic membrane (e.g. the ear drum) and ahead of the inner ear. It should also be noted that access to the inner ear may be accomplished through the endolymphatic sac/endolymphatic duct and the otic capsule. The inner ear tissues are of minimal size, and generally accessible through microsurgical procedures. Exemplary medicines which are typically used to treat inner ear tissues include but are not limited to urea, mannitol, sorbitol, glycerol, xylocaine, epinephrine, immunoglobulins, sodium chloride, steroids, heparin, hyaluronidase, aminoglycoside antibiotics (streptomycin/gentamycin), and other drugs, biological materials, and pharmaceutical compositions suitable for treating tissues of the human body. Likewise, treatment of inner ear tissues and/or fluids may involve altering the pressure, volumetric, and temperature characteristics thereof. Imbalances in the pressure levels of such fluids can cause various problems, including but not limited to conditions known as endolymphatic hydrops, endolymphatic hypertension, perilymphatic hypertension, and perilymphatic hydrops as discussed in greater detail below.

Delivery of therapeutic agents to the inner ear of a subject can be done by contact with the inner ear or through the external auditory canal and middle ear, as by injection or via catheters, or as exemplified in U.S. Pat. No. 5,476,446, which provides a multi-functional apparatus specifically designed for use in treating and/or diagnosing the inner ear of a human subject. The apparatus, which is useful in the practice of the present invention, has numerous functional capabilities including but not limited to (1) delivering therapeutic agents into the inner ear or to middle-inner ear interface tissues; (2) withdrawing fluid materials from the inner ear; (3) causing temperature, pressure and volumetric changes in the fluids/fluid chambers of the inner ear; and (4) enabling inner ear structures to be electrophysiologically monitored. In addition, other systems may be used to deliver the factors and formulations of the present invention including but not limited to an osmotic pump which is described in Kingma, G. G., et al., "Chronic drug infusion into the scala tympani of the guinea pig cochlea", *Journal of Neuroscience Methods,* 45:127–134 (1992). An exemplary, commercially-available osmotic pump may be obtained from the Alza Corp. of Palo Alto, Calif. (USA). U.S. Pat. No. 4,892,538, provides an implantation device for delivery of the factors and formulations of the invention. Cells genetically engineered to express FGF-2, or IGF-1, or their combination, and optionally, enhancing or augmenting factors or therapeutics (e.g., trkB or trkC agonist), can be implanted in the host to provide effective levels of factor or factors. The cells can be prepared, encapsulated, and implanted as provided in U.S. Pat. Nos. 4,892,538, and 5,011,472, WO 92/19195, WO 95/05452, or Aeischer et al., *Nature* 2:696–699 (1996), for example. U.S. Pat. No. 5,350,580 exemplifies a device comprising a biodegradable support incorporating a therapeutically effective releasable amount of at least one such active agent suitable for use in the invention; the device being surgically inserted into the middle ear where it is capable of providing extended release of active agent to the middle ear.

IGF-1, FGF-2, or agonist are also suitably administered together by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers,* 22:547–556 [1983]), poly(2-hydroxyethyl methacrylate) (Langer et al., *J. Biomed. Mater. Res.,* 15:167–277(1981), and Langer, *Chem. Tech.,* 12:98–105 (1982)), ethylene vinyl acetate (Langer et al., supra) or poly-D-(-)-3-hydroxybutyric acid (EP 133,988). Sustained-release IGF-1 compositions also include liposomally entrapped IGF-1. Liposomes containing IGF-1 are prepared by methods known per se: DE 3,218,121; Epstein et al., *Proc. Natl. Acad. Sci. U.S.A.,* 82:3688–3692(1985); Hwang et al., *Proc. Natl. Acad. Sci. U.S.A.,* 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the optimal IGF-1 and FGF-2 therapy.

For parenteral administration, in one embodiment, the IGF-1, FGF-2, or agonist are formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-1, FGF-2, or agonist each uniformly and intimately with liquid carriers or finely divided solid carriers or both. The carrier can be a parenteral carrier, more preferably a solution that is isotonic with the blood of the recipient, and even more preferably formulated for local administration to the inner ear. Examples of carrier vehicles include water, saline, Ringer's solution, a buffered solution, and dextrose solution. Non-aqueous vehicles such as fixed oils and ethyl oleate are also useful herein. The carrier suitably contains minor amounts of additives such as substances that enhance isotonicity and chemical stability, and when locally administered are non-toxic to the cells and structures of the ear, particularly the inner ear. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethyleneglycol (PEG); and/or neutral salts, e.g., NaCl, KCl, $MgCl_2$, $CaCl_2$, etc.

The IGF-1 and FGF-2 are typically formulated in such vehicles at a pH of from or about 4.5 to 8. Full-length IGF-1 is generally stable at a pH of no more than about 6.5, and is preferably formulated at pH 5 to 5.5; des(1-3)-IGF-1 is stable at from or about 3.2 to 5. It will be understood that use of certain of the foregoing excipients, carriers, or stabilizers will result in the formation of IGF-1 or insulin salts. The final preparation can be a stable liquid or lyophilized solid. A preferred stabilizer is benzyl alcohol or phenol, or both, and a preferred buffered solution is an acetic acid salt buffered solution. Trehalose and mannitol are also preferred stabilizers. More preferably, the osmolyte is sodium chloride and the acetic acid salt is sodium acetate. Additionally, the formulation can contain a surfactant, preferably polysorbate or poloxamer.

An "osmolyte" refers to an isotonic modifier or osmotic adjuster that lends osmolality to the buffered solution. Osmolality refers to the total osmotic activity contributed by ions and non-ionized molecules to a solution. Examples include inorganic salts such as sodium chloride and potassium chloride, mannitol, PEG, polypropylene glycol, glycine, sucrose, trehalose, glycerol, amino acids, and sugar alcohols such as mannitol known to the art that are generally regarded as safe (GRAS). The preferred osmolyte herein is sodium chloride or potassium chloride, particularly when locally administered.

The "stabilizer" is any compound that functions to preserve the active ingredients in the formulation, i.e., FGF-2 and IGF-1, so that they do not degrade or otherwise become inactive over a reasonable period of time or develop pathogens or toxins that prevent their use. Examples of stabilizers include preservatives that prevent bacteria, viruses, and fungi from proliferating in the formulation, anti-oxidants, or other compounds that function in various ways to preserve the stability of the formulation.

For example, quaternary ammonium salts are useful stabilizers in which the molecular structure includes a central nitrogen atom joined to four organic (usually alkyl or aryl) groups and a negatively charged acid radical. These salts are useful as surface-active germicides for many pathogenic non-sporulating bacteria and fungi and as stabilizers. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of stabilizers include aromatic alcohols such as phenol and benzyl alcohol, alkyl parabens such as methyl or propyl paraben, and m-cresol.

Typically, the stabilizer can be included in a stable liquid form of the formulation, but not in a lyophilized form of the formulation. In the latter case, the stabilizer is present in the bacteriostatic water for injection (BWFI) used for reconstitution. However, trehalose or mannitol, or the like can be, and are preferably, present in the lyophilized form. The surfactant is also optionally present in the reconstitution diluent.

The "inorganic salt" is a salt that does not have a hydrocarbon based cation or anion. Examples include sodium chloride, ammonium chloride, potassium chloride, magnesium chloride, calcium chloride, sodium phosphate, calcium phosphate, magnesium phosphate, potassium phosphate, ammonium phosphate, sodium sulfate, ammonium sulfate, potassium sulfate, magnesium sulfate, calcium sulfate, etc. Preferably, the cation is sodium and the anion is chloride or sulfate, and the most preferred inorganic salt is potassium chloride or sodium chloride.

The "surfactant" acts to increase the solubility of the IGF-1 and FGF-2 at a pH from or about 4 to 7. It is preferably a nonionic surfactant such as a polysorbate, e.g., polysorbates 20, 60, or 80, a poloxamer, e.g., poloxamer 184 or 188, or any others known to the art that are GRAS. More preferably, the surfactant is a polysorbate or poloxamer, more preferably a polysorbate, and most preferably polysorbate 20.

The "buffer" may be any suitable buffer that is GRAS and generally confers a pH from or about 4.8 to 8, preferably from or about 5 to 7, more preferably from or about 5 to 6, on the NPH insulin+IGF-1 formulation, and preferably a pH of from or about 5 to 6, more preferably from or about 5 to 5.5, on the IGF-1 formulation. Examples include acetic acid salt buffer, which is any salt of acetic acid, including sodium acetate and potassium acetate, succinate buffer, phosphate buffer, citrate buffer, histidine buffer, or any others known to the art to have the desired effect. The most preferred buffer is sodium acetate, optionally in combination with sodium phosphate.

The final formulation, if a liquid, is preferably stored at a temperature of from or about 2 to 8° C. for up to about four weeks. Alternatively, the formulation can be lyophilized and provided as a powder for reconstitution with water for injection that is stored as described for the liquid formulation.

U.S. Pat. No. 5,482,929, provides useful stabilized FGF-2 compositions which contain an aluminum salt of cyclodextrin sulfate to stabilize FGF. Recombinant human basic fibroblast growth factor (FGF-2) can be used at a concentration of greater than 0.1 ng/ml, preferably from about 0.5–40 ng/ml, and more preferably at about 2 ng/ml, particularly when used in vitro.

IGF-1 and FGF-2 to be used for therapeutic administration are preferably sterile. Sterility is readily accomplished by filtration through sterile filtration membranes (e.g., 0.2 micron membranes). Therapeutic IGF-1 and FGF-2 compositions generally are placed into a container having a sterile access port, for example, an intravenous solution bag or vial having a stopper pierceable by a hypodermic injection needle.

The IGF-1 and FGF-2 can be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered 1% (w/v) aqueous IGF-1 and FGF-2 solutions, and the resulting mixture is lyophilized. The infusion solution is prepared by reconstituting the lyophilized IGF-1 and FGF-2 using bacteriostatic Water-for-Injection.

The compositions herein also can suitably contain other growth factors, most preferably auditory or vestibular neuronal cell growth factors, or combination of factors, or other hair cell regeneration factors, for example retinoic acid or retinoic acid in combination with TGF-α. Such growth factors, including peptide growth factors, are suitably present in an amount that is effective for the purpose intended, e.g., to promote survival, growth, proliferation, regeneration, restoration or recovery of neuronal cells when desired, and optionally, to enhance growth or recovery of auditory or vestibular neurons.

The effectiveness of treating hearing impairments with the methods of the invention can be evaluated by the following signs of recovery, including recovery of normal hearing function, which can be assessed by known diagnostic techniques including those discussed herein, and normalization of nerve conduction velocity, which is assessed electrophysiologically.

In another embodiment, agonist compositions of the invention are used during clinical organ implants or transplants to keep or improve viability of inner ear hair cells. Preferably a combination of a factors will be used as taught herein, including a trkB and a trkC agonist, with the implant or transplant.

Kits are also contemplated for this invention. A typical kit would comprise a container, preferably a vial, for the IGF-1 formulation comprising IGF-1 in a pharmaceutically acceptable buffer, and/or a container, preferably a vial, comprising pharmaceutically acceptable FGF-2, and instructions, such as a product insert or label, directing the user on the use of the containers, particularly to combine the contents of the two containers, i.e., the two formulations, to provide a pharmaceutical formulation. Preferably, the pharmaceutical formulation is for treating a hearing impairment.

In the present experiments as provided in the Examples section herein, intact utricular epithelial sheets separated using a combined enzymatic and mechanical method essentially contain only supporting cells and hair cells (Corwin et al., 1995). The epithelial identity of the cultured cells was confirmed using various specific cell markers. While these cells expressed epithelial antigens including the tight junction protein (ZO1), cytokeratin and F-actin, they did not express fibroblast antigens, vimentin and Thy1.1, or glial and neuronal antigens. Most of the hair cells (stereocilliary bundle-bearing cells) were injured and many of them were dead after 2 days in culture due to their sensitivity to enzymatic digestion and mechanical trituration. Therefore, these cultures essentially represented a population of utricular supporting cells which are the progenitors for hair cells (Corwin and Cotanche, 1988; Balak et al., 1990; Rapheal, 1992; Weisleder and Rubel, 1992). These cultures provide an in vitro system to study proliferation and differentiation of the inner ear supporting cells.

The cultured inner ear epithelial cells required cell-cell contacts with neighboring epithelial cells to survive and proliferate. Initial attempts to culture completely-dissociated epithelial cells led to virtually all cells dying. A requirement of cell-cell contact for the survival and proliferation of epithelial progenitors is not unprecedented and has been observed previously with brain germinal zone progenitor cells (Gao et al., 1991) and E9 rat neuroepithelial cells (Li et al., 1996). The fact that proliferation of neuroepithelial cells only occurs within the highly compact CNS ventricular zone in vivo, and in the progenitor reaggregates (Gao et al., 1991) or neurospheres (Reynolds and Weiss, 1992) in vitro, suggests the existence of a membrane-bound factor for the growth of neuroepithelial cells. Consistent with this idea, membrane bound components from a C6 glioma cell line have been shown to be necessary for the proliferation and survival of dissociated, single cortical progenitor cells (Davis and Temple, 1994). In contrast to the organ culture (Warchol and Corwin, 1993), the partially dissociated epithelial cells grew poorly in serum-free medium, suggesting that in addition to the membrane bound molecules, soluble factors in the serum also promote the growth of these cells. A monolayer of fibroblast cells was reported as sufficient to support the growth of completely-dissociated chick cochlear epithelial cells (Finley and Corwin, 1995).

It is noted that the utricular epithelium is composed of a central, sensory epithelium and a peripheral, marginal zone (Lambert 1994). Efforts were made herein to collect only the sensory epithelium during dissections. In the initial experiments, however, a small portion of some of the transitional cells located at the border of the sensory epithelium and the marginal zone might also have been included because of the difficulty in completely removing them from the small, fragile epithelial sheets. Suspension of the partially dissociated epithelial sheets allowed uniform aliquoting of these cells into culture wells. The data obtained reflects mainly the proliferation of sensory epithelial cells although a small portion of the transitional epithelial cells may also contribute to a small extent. While the epithelial cells from the two domains could be derived from the same precursors (for example, the prosensory cells, see Kelley et al., 1993) during embryogenesis, they likely play a different role during hair cell differentiation or regeneration. Presumably, the cells in the sensory epithelium are more differentiated than those in the marginal area because the central hair cells appear earlier during development than the peripheral hair cells in the utricular sensory epithelium (Sans and Chat, 1982). Nevertheless, previous experiments (Lambert, 1994) have reported that upon exposure to aminoglycosides or induction by TGF-α, equivalent proliferation is observed in both sensory and marginal domains of the utricular epithelium.

As disclosed in the Examples herein, the sensory epithelium have been dissected completely free of the peripheral, non-sensory epithelial cells (though much fewer cells are obtained and plated in the culture wells). Essentially the same mitogenic effects of FGF-2, IGF-1, EGF and TGF-α were obtained as in the initial experiments. The cpm of tritiated thymidine incorporation was as follows: control= 671±92; FGF-2 treated=1787±221; IGF-1 treated= 1592±174; EGF treated=1168±130; TGF-α treated= 1483±109 (n=10 per group).

The pure epithelial cell culture, along with the tritiated thymidine assay, was a rapid and convenient method to evaluate effects of growth factors on proliferation of the inner ear epithelial progenitor cells. A large panel of agents could be and were examined in a relatively short time. The results of the tritiated thymidine assays were supported by the BrdU immunocytochemistry data. In the present experiments, several FGF family members, namely IGF-1, IGF-2, TGF-α and EGF, were mitogenic factors for the proliferation of utricular supporting cells, from among 30 growth factors.

The present cultures also prove useful for directly studying hair cell differentiation as increasing efforts are made toward discovery or development of early hair cell markers (Holley and Nishida, 1995). Testing agents for progenitor cell proliferation and hair cell differentiation is greatly facilitated and simplified in the pure utricular epithelial cell culture disclosed herein, as compared to in vivo or the organ culture: For example, it will now be possible in light of the present invention, to use specific inhibitors or activators in these cultures to further dissect the signal transduction pathways of a given growth factor involved in hair cell differentiation.

While the observations herein of the mitogenic effects of TGF-α and EGF are consistent with previous reports (Lambert, 1994; Yamashita and Oesterle, 1995), the results of several FGF family members, IGF-1, IGF-2 and combination of FGF-2 and TGF-α or IGF-1 are novel and surprising. These latter findings are in contrast to a study reported by Yamashita and Oesterle (1995) in the intact organ culture. One possibility for the discrepancy between these results is that the deprivation of hair cells in the present dissociated utricular epithelial cell cultures might trigger the upregulation of FGF and IGF-1 receptors and enhance the response to FGFs and IGF-1. If so, this likely reflects the situation occurring during inner ear injury or assault. Recently, Lee and Cotanche (1996) reported that damaging chicken cochlear epithelium by noise results in an upregulation of mRNA for the FGF receptor in the supporting cells. Finley and Corwin (1995) reported that FGF-2 promotes the proliferation of chick cochlear supporting cells which were completely dissociated and plated on a monolayer of fibroblast cells. The presence of high levels of FGF receptor and IGF-1 receptor in the inner ear epithelial cells after deprivation of hair cells and the inhibition of cell proliferation by neutralizing antibodies against either FGF-2 or IGF-1 support the idea that FGF-2 and IGF-1 act directly on the inner ear supporting cells and induce their proliferation following the removal of hair cells. FGF-2 and IGF-1 may be candidate molecules regulating proliferation of the inner ear supporting cells, particularly during hair cell regeneration following challenge by aminoglycosides or noise.

Alternatively, there may be a developmental response change to growth factors including FGF-2 and IGF-1 during maturation of the inner ear epithelium. It is possible that the mature inner ear epithelium responds differently relative to the developing epithelium. Exogenously added FGF-2 or IGF-1 might not elicit a proliferation in the intact, mature utricles (Yamashita and Oesterle, 1995) or in chick tissues which are treated with a very low concentration of aminoglycoside (1 nM, Oesterle et al., 1996) as they would in the immature utricles. Upon intensive damage by noise or drugs (massive degeneration of hair cells), the immature epithelium might be triggered to go back to an earlier developmental stage. Such injury induced status shift has been noticed for developing neurons (Gao and Macagno, 1988). The present study is performed on postnatal rat inner ear cells which are still undergoing maturation, but nonetheless is believed probative to the influence of FGF-2 and IGF-1 on hair cell regeneration after acoustic trauma or exposure to high doses of aminoglycosides in adult mammals.

It is intriguing that while several of the FGF family members are mitogenic, FGF-1 and FGF-5 elicit no detectable effects. Because there are at least 4 various subtypes of FGF receptors and different splicing forms of the receptors (Johnson and Williams, 1993), it is not known which of the subreceptors mediates the signal transduction pathway. It is particularly interesting to note the lack of an effect by FGF-1, which is present in spiral ganglion and proposed to be a trophic factor for hair cells (Pirvola et al., 1995).

It was previously reported that IGF-1 stimulates proliferative growth of otic vesicles at the early stages of ontogenesis (Leon et al., 1995). The work reported herein indicates that, in addition, IGF-1 regulates the development of inner ear epithelium at a slightly later stage—the stage of supporting cell proliferation. Because IGF-1 has been shown to act at multiple stages during the development of neurons, including proliferation (Gao et al., 1991), differentiation and survival (Neff et al., 1993: Beck et al., 1995), it should be interesting to determine whether it acts also at later stages of hair cell development or works coordinately together with other growth factors. A preliminary study by Gray et al. (1996) reported that IGF-1 protects hair cells from aminoglycoside-induced apoptosis. Because IGF-1 receptor is expressed by the cultured utricular epithelial cells (FIG. 5), it is likely that IGF-1 acts on IGF-1 receptor. However, a possibility of cross-reaction of IGF-1 through insulin receptor cannot be ruled out since insulin also elicits a mitogenic effect (data not shown).

The finding that utricular epithelial cells express FGF-2 and its receptor indicates that FGF-2 is a physiological growth factor for the development, maintenance and/or regeneration of hair cells. FGF-2 may exert its action through an autocrine mechanism. In this model, FGF-2 produced from hair cells may provide their own trophic support. Recent studies have suggested that cell differentiation and survival in the nervous system can be regulated by a growth factor-mediated autocrine interaction. For instance, colocalization of neurotrophins and their mRNAs is found in developing rat forebrain (Miranda et al., 1993) and a BDNF autocrine loop regulates the survival of cultured dorsal root ganglion cells (Acheson et al., 1995) Low et al. (1995) suggested that FGF-2 protects postnatal rat cochlear hair cells from aminoglycoside induced injury. Alternatively, a paracrine action might also be postulated in which FGF-2 synthesized by hair cells could locally influence maintenance of neighboring hair cells and proliferation of supporting cells. In this case, degeneration of hair cells may lead to a burst release of FGF-2, which would in turn stimulate supporting cell proliferation in the inner ear epithelium. The latter hypothesis may explain the supporting cell proliferation following hair cell death due to acoustic trauma or exposure to aminoglycosides, since FGF-2 does not have a signal sequence and cell injury is a major way for its release. The data herein that anti-FGF-2 antibody, but not anti-TGF-α antibody, significantly inhibits cell proliferation (FIG. 7) supports this hypothesis to a certain extent. The partial, but not complete, blocking effect by anti-FGF-2 antibody could be attributable to possible existence of other mitogens in the culture, loss of FGF-2 (due to hair cell injury) during the dissociation process and/or relief from contact inhibition within the epithelium following dissociation.

Neurotrophins including NGF, BDNF, NT-3 and NT-4/5 are important molecules for the development of the nervous system. In particular, BDNF and NT-3 are reported to be survival factors for spiral and vestibular ganglion neurons in vivo and in vitro (Zheng et al., 1995a, 1995b). These molecules also protect the two types of neurons against ototoxins in culture (Zheng et al., 1995a, 1995b). They are not, however, critical for the survival of hair cells (Ernfors et al., 1995; Fritzsch et al., 1995) and do not protect hair cells against ototoxins (Zheng and Gao, 1996). The present observations indicate that the neurotrophins do not directly affect the proliferation of the progenitor cells, but this does not rule out the possibility that they exert some effect on the later stages of hair cell differentiation. A certain degree of abnormality in the phenotype of type 1 utricular hair cells and the thickness of the utricular epithelium has been observed in the mice lacking both the BDNF and NT-3 genes (Ernfors et al., 1995) or those lacking both the trkB and trkC genes (Minichiello et al., 1995). In addition, a stage-specific effect of neurotrophins has been illustrated in the development of cerebellar granule cells. There, specific neurotrophins act at a late stage of differentiation but not at the stage of proliferation (Gao et al., 1995).

Similar to neurotrophins, many other growth factors examined in the present experiments do not show significant mitogenic effects on utricular supporting cells. They could, however, still be involved in later phases of hair cell regeneration. For example, retinoic acid can induce formation of supernumerary hair cells in the developing cochlea without involvement of cell proliferation (Kelley et al., 1993). On the other hand, early differentiating factors might inhibit the progenitor proliferation and push the progenitors to come out the cell cycle and become postmitotic cells. Regarding this aspect, it is interesting to note then that TGF-$\beta$1, TGF-$\beta$2, TGF-$\beta$3 and TGF-$\beta$5 exhibit an inhibition on the proliferation of the inner ear epithelial cells. Whether such observation implies a possible involvement of TGF-$\beta$s in the differentiation of hair cells remains to be determined.

The finding that FGF-2 and IGF-1 or TGF-$\alpha$ have additive mitogenic effects suggests that several growth factors may work in concert during the development of hair cells. For example, FGF-2 and TGF-$\beta$1 have been shown to synergistically regulate chondrogenesis during otic capsule formation (Frenz et al., 1994). There could be inhibitory signals coming from hair cells which would prevent supporting cell proliferation and induce new hair cell differentiation. It is quite possible that multiple growth factors may contribute together to the differentiation or regeneration of hair cells. They may work either in a sequential manner or at multiple steps. A combination of TGF$\alpha$, IGF-1 and retinoic acid will facilitate the utricular hair cell repair or regeneration.

In summary, we have established a purified mammalian utricular epithelial cell culture, which allowed rapid examination of effects of growth factors on supporting cell proliferation, an early phase during normal development and regeneration of new hair cells. Among the 30 growth factors we examined, FGF-2 is the most potent mitogen. The observation that the inner ear hair cells produced FGF-2 in vivo and utricular epithelial cells expressed FGF receptor in vitro suggest a physiological role of FGF-2 in hair cell development, maintenance or regeneration.

The following examples are offered by way of illustration and not by way of limitation. The disclosures of all citations in the specification are expressly incorporated herein by reference.

EXAMPLES

Example I

Characterization of Hair Cells

Cultured utricular epithelial cells were determined to express features of epithelial cells, but not those of fibroblast, glial or neuronal cells.

Utricular epithelial sheets were separated from postnatal day 4–5 (P4-5) Wistar rats using 0.5 mg/ml thermolysin (Sigma; in Hank's calcium and magnesium-free balanced salt solution) for 30 min at 37° C., based on the method reported previously (Corwin et al., 1995). The epithelial sheets (see FIG. 1A) were then incubated in a mixture of 0.125% trypsin and 0.125% collagenase for 8 min at 37° C. The enzyme activity was inactivated with a mixture of 0.005% soybean trypsin inhibitor (Sigma) and 0.005% DNase (Worthington) before being pipetted up and down with a 1 ml pipette tip 10 times in 0.05% DNase in BME. In this way, the epithelial sheets were partially dissociated into small pieces containing approximately 10–80 cells (FIG. 1B). Since we found that these cells grew very poorly in serum-free medium, a 5% fetal bovine serum-supplemented medium was used. The cell suspension was finally plated in polylysine (500 $\mu$g/ml) coated 96-well plate (for tritiated thymidine assays) or 16-well LabTek slides (for BrdU labeling and other immunocytochemistry) in 200 $\mu$l of serum-containing medium (DMEM plus 5% fetal bovine serum, 4.5 mg/ml glucose, 2 mM glutamine, 25 ng/ml fungizone and 10 units/ml penicillin) at a density of approximately 70 cells/mm$^2$. Typically, cells prepared from 4 litters of pups (40 P4-5 rats) were equally aliquoted into 80 wells.

While most isolated single cells died after 2 days in culture, the cell clumps containing approximately 10–80 cells survived well and grew in patches in the serum-supplemented medium (FIG. 1C). Immunocytochemical staining with different types of cell markers revealed that these cultured cells expressed epithelial cell antigens including a tight junction protein (ZO1, FIG. 1E), F-actin (FIG. 1F) and cytokeratin (FIG. 1G). They did not express antigens for other types of cells, such as glial filament protein (GFAP), the oligodendrocytoantigen (myelin), neurofilament protein or fibroblast antigens, vimentin (FIGS. 1C, 1D) and Thy1.1. These results are summarized in Table 1.

TABLE 1

Immunocytochemical characterization of the cultured utricular epithelial cells

| Markers | Immunopositivity |
|---|---|
| General epithelial cell antigens | |
| ZOI (Tight junction protein) | + |
| F-actin | + |
| Cytokeratin | + |
| Fibroblast antigen | |
| Vimentin | – |
| Thy 1.1 | – |
| Glial cell antigen | |
| GFAP | – |
| Myelin (Oligodendrocyte antigen) | – |
| Neuronal antigen | |
| NF | – |

Utricular epithelial cells were prepared from P4-5 rats and plated in polylysine-coated 16-well Lab-Tek culture slides in 5% FBS-supplementedmedium for 48 hr. The cultures were fixed with 4% paraformaldehydeand were then stained with a phalloidin-FITC conjugate or antibodies listed above.

These results suggest that the cultured cells are pure epithelial cells. As revealed by phalloidin staining (FIG. 1F), few stereocilliary bundle-bearing cells (hair cells) were seen, suggesting that majority of the hair cells were injured and many of them might be dead after 2 days in culture under the present culture condition. At present, we do not have specific markers for hair cells or supporting cells. Because the utricular epithelial sheets contained mainly supporting cells and hair cells, the vast majority of the surviving cells in the cultures represented a population of utricular supporting cells.

Example II

Stimulation of Hair Cell Regeneration

To examine whether any of the presently known growth factors stimulate proliferation of the utricular supporting cells, we measured DNA synthesis using tritiated thymidine incorporation assays. To measure DNA synthesis, ³H-thymidine (2 μCi/well) was added for 24 hr at 24 hr of culture, and cells were harvested using a Tomtec cell harvester. Because the epithelial cells were grown on a polylysine substrate, trypsin (1 mg/ml) was added to the culture wells for 25 min at 37° C. to lift the cells before cell harvest. Cpm/well were then counted with a matrix 9600 gas counter (Packard Instrument Company, IL) as described previously (Gao et al., 1995). Data was collected from 5 or 10 culture wells from each of the experimental groups and expressed as mean±s.e.m. Two-tailed, unpaired t-test was used for statistical analysis. Under control culture conditions, a moderate level of thymidine uptake was detected.

Members of the FGF family including FGF-1, FGF-2, FGF-4, FGF-5, FGF-6 and FGF-7 (R & D Systems), IGF-1, IGF-2 (R & D Systems), TGF-α (R & D Systems), EGF (Collaborative Research), human recombinant neurotrophins (Genentech), TGF-β1 (Genentech), TGF-β2, TGF-β3, TGF-β5 (R & D Systems), activin, inhibin, glial cell derived neurotrophic factor (GDNF), heregulin, Gas-6, vascular endothelial growth factor (VEGF), ciliary neurotrophic factor (CNTF), leukemia inhibitory factor (LIF), cardiotrophin-1, c-kit ligand (Genentech), platelet-derived growth factor (PDGF) (Gibco) and retinoic acid (Sigma) were added to the cultures at the time when the cells were plated. Maximal effects for FGF-2, IGF-1 and TGF-α were seen at 100 ng/ml (0.1–100 ng/ml tested), and therefore all growth factors were used at a concentration of 100 ng/ml, except TGF-β1, TGF-β2, TGF-β3 and TGF-β5 which were tested at 1 ng/ml, and neurotrophins at 20 ng/ml (Zheng et al., 1995a). The concentration of retinoic acid was $10^{-8}$ M (Kelley et al., 1993).

When several FGF family members including FGF-2, FGF-4, FGF-6 and FGF-7 were added to the culture, a significant elevation in thymidine uptake was seen (p<0.05; FIG. 2). Among them, FGF-2 was the most potent mitogen. In contrast, FGF-1 and FGF-5 did not show a significant effect (p>0.05; FIG. 2). Inclusion of IGF-1 and IGF-2 in the cultures also significantly increased thymidine incorporation (p<0.05). As positive controls, we added TGF-α or EGF, two previously reported mitogens for the supporting cells (Lambert, 1994, Yamashita and Oesterle, 1995), to the cultures. DNA synthesis was enhanced approximately 1.7-fold and 1.5-fold by TGF-α and EGF, respectively (FIG. 2).

To determine whether the elevation in the thymidine uptake reflected an increase in number of dividing cells, we performed bromo-deoxyuridine (BrdU) immunocytochemistry. BrdU labeling was carried out using a previously reported method (Gao et al., 1991). Briefly, after 1 day in culture, BrdU (1:400; Amersham cell proliferation kit) was added to the culture medium for 24 h. The cultures were fixed in 4% paraformaldehyde (30 min), treated with 2 N HCl (40 min), and incubated with an anti-BrdU monoclonal antibody (Becton-Dickinson, 1:40 in phosphate buffered saline containing 0.1% Triton-X100) overnight at 4° C. The cultures were then processed with a Vector ABC kit. After diaminobenzidine-peroxidase reaction, the cells were dehydrated with ethanol, cleared in Histoclear (American Histology) and mounted in Permount (Fisher). BrdU-positive cells were counted from the entire areas of 10 or more culture wells for each of the experimental groups. Data was expressed as mean±s.e.m. Two-tailed, unpaired t-test was used for statistical analysis.

As shown in FIG. 3, a much greater number of BrdU-positive cells were seen in the cultures containing FGF-2. Cell counts performed from the control cultures and cultures containing 100 ng/ml FGF-2 confirmed that FGF-2 significantly enhanced proliferation of the utricular supporting cells (p<0.01, Table 2). A significantly higher number of BrdU-positive cells were also seen in the cultures containing 100 ng/ml IGF-1 (p<0.05) or TGF-α (P<0.01) as compared to the control cultures (Table 2).

TABLE 2

Cell counts of BrdU-positive cells in the utricular epithelial cell cultures

| Experimental groups | BrdU-positive cells/culture |
| --- | --- |
| Control | 218 ± 29 |
| FGF-2 | 795 ± 32** |
| IGF-1 | 367 ± 30* |
| TGF-α | 421 ± 16** |
| FGF-2 + IGF-1 | 940 ± 47** |
| FGF-2 + TGF-α | 1051 ± 40** |

Utricular epithelial cells were prepared from P4-P5 rats and cultured in polylysine-coated 16-well Lab-Tek culture slides in control medium or in medium containing FGF-2, TGF-α, IGF-1, or a combination of FGF-2 and TGF-α or IGF-1 at a concentration of 100 ng/ml for 48 hr. BrdU was added at the 24 hr of the culture for 24 hr. The cultures were fixed with 4% paraformaldehyde and were then immunostained with antibodies against BrdU. Cell counts of BrdU positive cells were performed as described in Materials and Methods. Data collected from 10 or more cultures for each of the experimental groups is expressed as mean ± s.e.m. As compared to the control cultures, the single asterisk indicates p < 0.05 and the double asterisks indicates p < 0.01. The cultures containing both FGF-2 and IGF-1 or FGF-2 and TGF-α show a significantly higher number of BrdU positive cells than the cultures containing FGF-2 alone (p < 0.05).

Example III

Comparison of Mitogens

To compare the potency of FGF-2 to IGF-1 and TGF-α, a dose-dependent study was carried out in the utricular epithelial cell cultures at a range of 0.1–100 ng/ml (FIG. 4). At a concentration of 0.1 ng/ml, none of the three growth factors showed a detectable effect (p>0.05). At a concentration of 1 ng/ml, FGF-2 displayed a significant mitogenic effect (P<0.01)whereas IGF-1 and TGF-α had no detectable effect. At higher doses (10–100 ng/ml), all three growth factors showed significant mitogenic effects (p<0.05) as compared to the control cultures. However, FGF-2 was more potent than IGF-1 or TGF-α (p<0.01, FIG. 4). The higher potency of FGF-2 than that of IGF-1 or TGF-α was also observed with BrdU immunocytochemistry (Table 2).

To determine whether FGF-2 and IGF-1 or TGF-α act synergistically, FGF-2 was added to the cultures together with either IGF-1 or TGF-α. Both tritiated thymidine incorporation and BrdU immunocytochemistry confirmed that combinations of FGF-2 and IGF-1 or FGF-2 and TGF-α resulted in a significantly higher cell proliferation (p<0.05, FIG. 2 and Table 2). FGF-2 was a more potent mitogen than IGF-1 or TGF-α.

In addition to FGF family members, IGF-1, IGF-2, TGF-α and EGF, many other growth factors have been reported to influence cell proliferation and differentiation. These include neurotrophins, the TGF-β superfamily, glial cell mitogens such as heregulin and Gas-6, endothelial cell mitogen such as VEGF, and others listed in Table 3. When examined in these cultures, none of the above-mentioned growth factors showed detectable mitogenic effects (p>0.05) on the utricular epithelial cells (Table 3). In fact, TGF-β1, TGF-β2, TGF-β3 and TGF-β5 showed a 30–67% inhibition of cell proliferation. Neurotrophins and other growth factors examined do not promote the proliferation of cultured utricular epithelial cells.

TABLE 3

Tritiated thymidine incorporation in utricular epithelial cell cultures containing different growth factors

| Experimental groups | cpm/culture (mean ± s.e.m.) |
| --- | --- |
| Control | 2461 ± 215 |
| Neurotrophins | |
| NGF | 2056 ± 106 |
| BDNF | 2352 ± 227 |
| NT-3 | 2259 ± 211 |
| NT-4/5 | 2296 ± 126 |
| TGF-β superfamily members | |
| TGF-β1 | 1524 ± 73 |
| TGF-β2 | 1729 ± 115 |
| TGF-β3 | 929 ± 126 |
| TGF-β5 | 807 ± 59 |
| Activin | 2383 ± 186 |
| Inhibin | 1959 ± 183 |
| GDNF | 2383 ± 186 |
| Schwann cell mitogens | |
| Heregulin | 2854 ± 179 |
| Gas-6 | 2588 ± 95 |
| Endothelial cell mitogen | |
| VEGF | 2156 ± 211 |
| PDGF | 2387 ± 299 |
| CNTF | 2918 ± 404 |
| LIF | 2003 ± 206 |
| Cardiotrophin-1 | 2065 ± 295 |
| c-kit ligand | 2729 ± 346 |
| Retinoic acid | 2466 ± 297 |

Utricular epithelial cells were prepared from P4-5 rats and plated in polylysine-coated 96-well plate in control medium or medium containing different growth factors (see Materials and Methods). $^3$H-thymidine (2 μCi/well) was added for 24 h at 24 h of culture, and cells were harvested using a Tomtec cell harvester. Cpm/well were then counted with a matrix 9600 gas counter as described in Material and Methods. Data was collected from 5 culture wells of each experimental group and is expressed as mean ± s.e.m. Note that no factors listed in the table exhibited significant mitogenic effects (P > 0.05), although inhibition of cell proliferation was induced by TGF-βs (P < 0.05).

Example IV
Cultured Utricular Epithelial Cells Express FGF Receptor and IGF-1 Receptor To provide further evidence that FGF family members and IGF-1 act directly on these epithelial cells, we did immunostaining using antibodies against FGF receptor and IGF-1 receptor on both utricular sections and the cultured epithelial cells prepared from P4-5 rats. After 2 days in culture, the cells were fixed in 4% paraformaldehyde (in 0.1 M phosphate buffer, pH 7.4) for 30 min. The preparations were first blocked with a 10% normal goat serum in 0.1% triton-X100 in phosphate buffered saline (PBS) for 20 min and then incubated with monoclonal antibodies (N52) against vimentin (10 μg/ml, Boehringer), Thy1.1 (1:200, Chemicon), neurofilament 200 kd (5 μg/ml, Boehringer), Myelin (1:200, Cedar Lane Laboratories) and pan-cytokeratin (1:50, Sigma), or rabbit antisera against a tight junction protein (ZO1, 1:200, Zymed) and GFAP (1:500, Dako) in PBS containing 3% normal goat serum and 0.1% Triton-X100 overnight at 4° C. FITC-conjugated secondary antibodies (1:200; Cappel) were then used to reveal the labeling patterns. To examine the staining pattern of F-actin, the preparations were incubated with 0.5 μg/ml phalloidin-FITC conjugates in PBS for 45 min at room temperature. To determine whether the cultured cells expressed receptors for growth factors, a monoclonal antibody against FGF receptor (1:200, Chemicon) and antisera against IGF-1 receptor b (1:1100, Santa Cruz Biotech.) and trkA (1:10,000, kindly provided by Dr. L. Reichardt at UCSF) were used as primary antibodies. FITC-conjugated secondary antibodies (1:200, Cappel) were used to reveal the staining patterns. While immunoreactivity was low in the sensory epithelium of the utricular sections (data not shown), many of the cultured utricular epithelial cells expressed high levels of the FGF receptor (FIGS. 5A, 5B) and the IGF-1 receptor (FIGS. 5C, 5D), presumably due to deprival of hair cells. In contrast, antiserum against TrkA, a high affinity receptor for NGF, did not stain the cultured cells (FIGS. 5E, 5F). These results suggest that the mitogenic effects of FGFs and IGF-1 are likely through activation of their high affinity binding receptors on these cultured cells.

Example V
Utricular Epithelial Cells Produce FGF-2 in vivo

To determine whether FGF-2 is physiologically present in the utricle, we performed immunohistochemistry with a monoclonal antibody against FGF-2 on P5 rat utricular sections. For immunohistochemistry, P5 rat utricles were fixed in 4% paraformaldehyde in 0.1 M phosphate buffer (pH 7.4) for 1 hr. The preparations were rinsed in PBS, cryoprotected in 30% sucrose solution and embedded in OCT. Twenty-five micrometer sections were cut and collected on a cryostat machine. The sections were then immunostained with a monoclonal antibody against FGF-2 (3 μg/ml, UBI) through a FITC-conjugated secondary antibody (1:200, Vector). Negative controls were performed by skipping the primary antibody step. The preparations were mounted in Fluoromount-G (Southern Biotech. Assoc., AL) which contains an anti-fading agent, and viewed using a Zeiss Axiophot epifluorescent microscope. As shown in FIG. 6, hair cells, but not supporting cells, in the utricular sensory epithelium expressed a moderate level of FGF-2. Such immunoreactivity was absent in the basilar membrane area. The FGF-2 antibody labeling was specific since no staining was seen when the utricular sections were incubated with only the secondary antibody. The in vivo expression of FGF-2 by hair cells in the utricular sensory epithelium suggests that FGF-2 is a physiological growth factor.

Example VI
Neutralizing Antibodies Against FGF-2 or IGF-1 Significantly Inhibited Utricular Epithelial Cell Proliferation To find out whether utricular cell proliferation could be blocked or inhibited by removal of endogenous FGF-2 or IGF-1 in the culture, we added neutralizing antibodies to the cultures. Partially dissociated P4-5 rat utricular sheets were plated in polylysine (500 μg/ml) coated 96-well plate in 100 μl of 1% FBS supplemented medium. Anti-FGF-2 (20 μg/ml, UBI), anti-IGF-1 (40 μg/ml, UBI), anti-TGF-α (20 μg/ml, R&D Systems) or anti-CNTF (20 μg/ml, R&D Systems) neutralizing antibody was added to the culture at the time of plating. $^3$H-thymidine (1 μCi/well) was added for 24 hr at 24 hr of culture, and cells were harvested as described above. Since these cells grew very poorly in serum free medium, we plated them in reduced fetal bovine serum (1%) supplemented medium. Under these conditions, the urticular epithelial cell proliferation was significantly inhibited by the presence of either anti-FGF-2 or anti-IGF-1 antibodies (p<0.01). In contrast, neither anti-TGF-α antibody nor anti-CNTF antibody which served as negative controls showed any inhibitory effect. The inhibition by anti-FGF-2 or anti-IGF-1 antibodies was partial (approximately 25%), presumably attributable to possible existence of other mitogens such as other FGF members, EGF and IGF-2 (see above) in the culture medium.

Nevertheless, these results provide further supporting evidence that there were endogenous FGF-2 and IGF-1 in the culture, which stimulated utricular epithelial cell proliferation. The inhibition of cell proliferation by anti-FGF-2 or anti-IGF-1 antibody was not due to a general toxicity because anti-TGF-α and anti-CNTF antibodies did not influence cell proliferation and the mitogenic activity of TGF-α was not affected in the presence of either anti-FGF-2 or anti-IGF-1 antibodies (FIG. 7).

CITED REFERENCES

1. Acheson et al., *Nature* 374:450–453 (1995).
2. Adler et al., *Assoc Res Otolaryngol Abstr*, p4 (1996).
3. Anderson, *Neuron* 3, 1–12 (1989).
4. Balak et al., *J Neurosci* 10:2505–2512 (1990).
5. Beck et al., *Neuron* 14:717–730 (1995).
6. Bianchi et al., *Assoc Res Otolaryngol Abstr*, p108 (1995).
7. Cattaneo et al., *Nature* 347:762–765 (1990).
8. Corwin et al., *Science* 240:1772–1774 (1988).
9. Corwin et al., *Assoc Res Otolaryngol Abstr*, 18:87 (1995).
10. Cotanche, *Hear Res* 30:181–196 (1987).
11. Cotanche et al., *Curr Opinion Neurobiol* 4:509–514 (1994).
12. Davis et al., *Nature* 372:263–266 (1994).
13. Ernfors et al., *Nature* 368:147–150 (1994).
14. Ernfors et al., *Neuron* 14:1153–1164 (1995).
15. Farinas et al., *Nature* 369:658–661 (1994).
16. Finley et al., *Assoc Res Otolaryngol Abstr*, p84 (1995).
17. Forge et al., *Science* 259:1616–1619 (1993).
18. Frenz et al., *Development* 120:415–424 (1994).
19. Fritzsch N et al., *Auditory Neurosci* 1:401–417 (1995).
20. Gao et al., *Neuron* 1: 269–277 (1988).
21. Gao et al., *Neuron* 6:705–715 (1991).
22. Gao et al., *J Neurosci* 15:2656–2667 (1995).
23. Ghosh et al., *Neuron* 15:89–103 (1995).
24. Gray et al., *Assoc Res Otolaryngol Abstr*, p198 (1996).
25. Holley et al (1995) *J Neurocytol* 24:853–864.
26. Johnson et al (1993) *Adv Cancer Res* 60:1–41.
27. Jones et al (1996) *J Neurosci* 16:649–662.
28. Kelley et al (1993) *Development* 119:1041–1053.
29. Kopke et al (1996) *Assoc Res Otolaryngol Abstr*, p198.
30. Lambert et al (1994) *Laryngoscope* 104:701–717.
31. Lee et al (1996) *Hear Res* 94:1–13.
32. Lefebvre et al (1994) *Neuroreport* 5:865–868.
33. Leon et al (1995) *Endocrinology* 136:3494–3503.
34. Li et al (1996) *Assoc Res Otolaryngol Abstr*, p7.
35. Li et al (1996) *Endocrine*, in press.
36. Low et al (1995) *Assoc Res Otolaryngol Abstr*, p200
37. Minichiello et al (1995) *Development* 121:4067–4075.
38. Miranda et al (1993) *Proc Natl Acad Sci USA* 90:6439–6443.
39. Neff et al (1993) *J Neurobiol* 24:1578–1588.
40. Oesterle et al (1996) *Assoc Res Otolaryngol Abstr*, p198.
41. Pirvola et al (1995) *Proc Natl Acad Sci USA* 92:9269–9273.
42. Rapheal et al (1992) *J Neurocytol* 21:663–671.
43. Reynold et al (1992) *Science* 255:1707–1710.
44. Ryals et al (1988) *Science* 240:1774–1776.
45. Sans et al (1982) *J Comp Neurol* 206:1–8.
46. Vicario-Abejon et al (1995) *Neuron* 15:105–114.
47. Warchol et al (1993) *Hear Res* 71:28–36.
48. Warchol et al (1993) *Science* 259:1619–1622.
49. Weisleder et al (1992) *Exp Neurol* 115:2–6.
50. Yamashita et al (1995) *Proc Natl Acad Sci USA* 92:3152–3155.
51. Zheng et al (1996) *Eur J Neurosci*, 8:1897–1905.
52. Zheng et al (1995a) *J. Neurosci.* 15:5079–5087.
53. Zheng et al (1995b) *J. Neurobiol.* 28:330–340.
54. Anniko et al (1986) *Am J Otolaryngol* 7:276–293.
55. Apfel et al (1991) *Ann. Neurol.* 29:87–89.
56. Ard et al. (1985) *Neurosci.* 16:151–170.
57. Au et al (1987) *Biochem Biophys Acta* 902:80–86.
58. Baired et al (1992) *J. Neurosic.* 12:619–634.
59. Barbacid et al (1993) *In Molecular Genetics of Nervous System Tumors*. (New York: Wiley-Liss), pp123–136.
60. Barde et al (1982) *EMBO J.* 1:549–553.
61. Bareggi et al (1990) *Pharmacol. Res.* 22:635–644.
62. Barker et al (1994) *Neuron* 13:203–215.
63. Berggren et al., (1990) *Acta Otolaryngol. (Stockh)* 109:57–65.
64. Berkemeier et al., (1991) *Neuron* 7:857–866.
65. Boettcher et al., (1989) *Hear Res* 42: 129–142.
66. Boettcher et al., (1990) *Arch Otolaryngol Head Neck Surg* 116:681–684.
67. Boettcher et al., (1991) *Am. J Otolaryngol* 12:33–47.
68. Carenza (1986) *Gynecol. Oncol.* 25:244–249.
69. Chao et al., (1986) *Science* 232:518–521.
70. Chao et al., (1992) *Cell* 68:995–997.
71. Clary et al., (1994) *Proc. Natl. Acad. Sci USA* 91:11133–11137.
72. Clary et al (1994) *Mol. Biol. Cell* 5:549–563.
73. Cohen et al., (1994) *J. Neurobiol.* 25:953–959.
74. Cordon-Cardo et al (1991) *Cell,* 66, 173–183
75. Corwin et al (1991) *Ann Rev Neurosci* 14: 301–333.
76. Cotanche et al., (1994) *Curr Opinion Neurobiol* 4: 509–514.
77. Davies et al., (1993) *Neuron* 11:565–574.
78. Davies et al (1993b) *J. Neurosci.* 13:4961–4967.
79. Davies et al., (1986)*Nature* 319:497–502.
80. De Moura et al (1968) *Arch Otolaryngol* 87:60–64.
81. Dublin et al., (1976): *C. C. Thomas*.
82. Duckert et al., *J. Comp. Neurol.* 331:75–96.
83. Ernfors et al (1990) *Proc. Natl. Acad. Sci. USA* 87:5454–5458.
84. Ernfors et al., (1994) *Nature* 368:147–150.
85. Ernfors et al., (1995) *Assoc. Res Otolaryngol Abstr* p190.
86. Escandon et al., (1994) *J. Neurosci.* 14:2954–2068.
87. Falbe-Hansen et al., (1941) *Acta Otolaryngol suppl* 44: 1–216.
88. Fariñas et al (1994). *Nature* 369:658–661.
89. Fischer et al (1994) *Proc. Natl. Acad. Sci. USA* 91:8607–8611.
90. Fleischman et al (1975) *Pharmacol.* 33:320–332.
91. Forge et al (1993) *Science* 259:1616–1619.
92. Fritzsch et al (1995) *Assoc. Res. Otolaryngol Abstr.* p190.
93. Furley et al (1990) *Cell* 61:157–170.
94. Gao et al (1991) *Neuron* 6:705–715.
95. Gao et al (1995b) *Ann Neurol* (1995) 38:30–37.
96. Gao et al (1995) *J. Neurosci.* 15:2656–2667.
97. Garner et al (1994) *Neuron* 13:457–472.
98. Gotz et al (1994) *Nature* 372:266–269.
99. Grof et al., *Eur. J. Biochem.* 204:745–749 (1992).
100. Guild et al (1931) *Acta Otolaryngol. (Stockh)* 15:269–308.
101. Hefti et al (1986) *J Neurosci* 6:2155–2162.
102. Hinojosa et al (1987) *J. Infect. Dis.* 156: 449–455.
103. Hohn et al (1990) *Nature* 344:339–341.
104. Hood et al., *Contemporary applications of neurobiology in human hearing assessment* (Raven Press, New York, 1986).
105. Hulme, et al., E. C. and Birdsall, M. J. M., *Strategy and Tactics in Receptor Binding Studies*, p63–212 in *Receptor-Ligand Interactions*, Ed. E. C. Hulme.

106. Hyman et al., (1991) *Nature* 350:230–233.
107. Hynes et al., (1994) *J. Neurosci. Res.* 37:144–154.
108. Ip et al., (1993) *Neuron* 110:137–149.
109. Ip et al (1992) *Proc. Nat. Acad. Sci. USA* 89:3060–3064.
110. Jarvis et al., (1966) *J Laryngol* 80: 318–320.
111. Jones et al., (1990) *Proc. Natl. Acad. Sci. USA* 87:8060–8064.
112. Kaplan et al., (1991) *Science* 252, 554–558
113. Kaplan et al., (1991) *Nature* 350:158–160.
114. Kelley et al., (1995) *J Neurosci* 15:3013–3026.
115. Kelley et al., (1993) *Development* 119:1041–1053.
116. Klein et al., (1991a) *Cell* 65:189–197.
117. Klein et al., (1991b) *Cell* 66:395–403.
118. Klein et al., (1990) *Development* 109:845–850.
119. Klein, et al., (1992) *Neuron* 8, 947–956
120. Klein, et al., (1989), *EMBO J.,* 8, 3701–3709
121. Knusel et al., (1992) *J Neurosci* 12:4391–4402.
122. Koliatsos et al., (1993) *Neuron* 10:359–367.
123. Konings et al., (1994) *Brain Res* 640:195–204.
124. Kopf-Maier et al., (1992) *Chem. Biol Interact* 82:295–316.
125. Korsching, et al., (1993) *J. Neurosci.* 13:2739–2748.
126. Lamballe et al., (1991) *Cell* 66:967–979.
127. Lambert et al., (1994) *Laryngoscope* 104:701–718.
128. Lärkfors et al., (1993) *Neurosci.* 19:A278.14.
129. Leake et al., (1992) *Hear Res* 64:99–117.
130. Lefebvre et al., (1994) *Neuro Report* 5:865–868.
131. Lefebvre, et al., (1993) *Science* 260:692–695.
132. Lefebvre et al., (1991) *Acta Otolaryngol (Stockh)* 111:304–311.
133. Lefebvre et al., (1995) *Science* 267: 709–711.
134. Leibrock et al., (1989) *Nature* 341:149–152.
135. Levi-Montalcini et al., (1987) *EMBO J.* 6:1145–1154.
136. Lim et al, (1986) *Am J Otolaryngol* 7:73–99.
137. Lippe et al., (1995) *Assoc Res Otolaryngol Abstr.* p84.
138. Maisonpierre et al., (1990) *Science* 247:1446–1451.
139. Martin-Zanca et al., (1989) *Mol. Cell. Biol.,* 9, 24–33.
140. McAlpine et al., (1990) *Hear Res* 47:191–204.
141. McCabe et al., (1965) *Ann Otol* 74: 312–324.
142. Mollman et al (1990) *N. Engl. J. Med.* 322:126–127.
143. Myers et al., (1965) *Arch Otolaryngol Head Neck Surg* 82: 483–493.
144. Nakai et al., (1982) *Acta Otolaryngol* 93:227–232.
145. Pirvola et al., (1992) *Proc. Natl. Acad. Sci. USA* 89:9915–9919.
146. Pryor et al, (1994) Chang L W, ed, Marcel Dekker, Inc. PP345–371.
147. Rastel et al., (1993) *J Neurosci Methods* 47:123–131.
148. Richardson et al., (1991) *Hear Res* 53:293–311.
149. Roelofs et al., (1984) *Neurology* 34:934–938.
150. Rosenthal et al., (1990) *Neuron* 4:767–773.
151. Rybak et al., (1986) In: *Neurobiology of Hearing.* Altschuler R A, Bobbin R P, Hoffman D W, Eds. Raven Press (New York) PP441–454.
152. Schacht et al., (1986) *Hear Res* 22: 297–304.
153. Schecterson et al., (1994) *Hear. Res.* 73:92–100.
154. Scopes et al., R., *Protein Purification,* Springer-Verlag, NY (1982)
155. Sera et al., (1987) *Scanning Microsc.* 1:1191–1197.
156. Shelton et al., (1995) *J. Neurosci.* 15:477–491.
157. Siegal et al., (1990) *Cancer* 66:1117–1123.
158. Snider et al., (1994) *Cell* 77:627–638.
159. Sobkowicz et al., (1975) *J. neurocytol.* 4:543–572.
160. Soppet et al., (1991) *Cell* 65:895–903.
161. Squinto et al., (1991) *Cell* 65:885–893.
162. Stadnicki et al., (1975) *Cancer Chemother. Rep.* 59:467–480.
163. Thompson et al., (1984) *Cancer* 54:1269–1275.
164. Tsoulfas et al., (1993) *Neuron* 10:975–990.
165. Tsue et al., (1994a) *Proc Natl Acad. Sci USA* 91:1584–1588.
166. Tsue et al., (1994b) *Head Neck Surg* 111:281–301.
167. Valenzuela et al., (1993) *Neuron* 10: 963–974.
168. Vazquez et al., (1994) *Anat. Embryol.* 189:157–167.
169. Verdi, et al., (1994) *Neuron* 12:733–745.
170. Von Bartheld et at., (1991) *Development* 113: 455–470.
171. Warchol et al., (1993) *Science* 259:1619–1622.
172. Weskamp et al., (1991) *Neuron* 6:649–663.
173. Wheeler et al., (1994) *Hear. Res.* 73:46–56.
174. Windebank et al., (1994) *Neurology* 44: 488–494.
175. Wittmaack et al., (1903) *Pflueger Arch Ges Physiol* 95:237.
176. Woodford et al., (1978) *Ann Otol Rhinol Laryngol* 87:117–127.
177. Yamashita et al., (1995) *Proc Natl Acad Sci USA* 92:3152–3155.
178. Yan et al., (1992) *Nature* 360:753–755.
179. Yan et al., (1994) *Exper. Neurology* 127:23–36.
180. Ylikoski et al., (1993) *Hear. Res.* 65:69–78.

What is claimed is:

1. A kit comprising:

(a) a container comprising, in a pharmaceutically acceptable carrier an inner-ear-supporting-cell-proliferation-inducing amount of one or more of the group consisting of insulin-like growth factor I (IGF-I), fibroblast growth factor-2 (FGF-2), an IGF-1 agonist and an FGF-2 agonist, and an effective amount of an agonist anti-tyrosine kinase B (trkB) antibody or an agonist anti-tyrosine kinase C (trkC) trkC antibody; and (b) instructions for using the contents of container (a) to treat an inner ear disorder.

2. The kit of claim 1, comprising an inner-ear-supporting-cell-proliferation-inducing amount of IGF-I.

3. The kit of claim 1, comprising an inner-ear-supporting-cell-proliferation-inducing amount of FGF-2.

4. The kit of claim 1, comprising an inner-ear-supporting-cell-proliferation-inducing amount of an IGF-I agonist.

5. The kit of claim 1, comprising an inner-ear-supporting-cell-proliferation-inducing amount of an FGF-2 agonist.

6. The kit of claim 1, wherein said effective amount of an agonist anti-trkB antibody or an agonist anti-trkC antibody comprises a trkB antibody.

7. The kit of claim 1, wherein said effective amount of an agonist anti-trkB antibody or an agonist anti-trkC antibody comprises a trkC antibody.

* * * * *